(12) United States Patent
Weissman et al.

(10) Patent No.: US 11,905,333 B2
(45) Date of Patent: *Feb. 20, 2024

(54) SELECTIVE IMMUNODEPLETION OF ENDOGENOUS STEM CELL NICHE FOR ENGRAFTMENT

(71) Applicant: The Board of Trustees of the Leland Stanford Junior University, Stanford, CA (US)

(72) Inventors: Irving L. Weissman, Stanford, CA (US); Agnieszka Czechowicz, Menlo Park, CA (US); Deepta Bhattacharya, San Francisco, CA (US); Daniel Kraft, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/087,618

(22) Filed: Dec. 22, 2022

(65) Prior Publication Data

US 2023/0128340 A1 Apr. 27, 2023

Related U.S. Application Data

(63) Continuation of application No. 16/035,187, filed on Jul. 13, 2018, which is a continuation of application No. 15/211,679, filed on Jul. 15, 2016, now Pat. No. 10,072,091, which is a continuation of application No. 12/447,634, filed as application No. PCT/US2007/083529 on Nov. 2, 2007, now abandoned.

(60) Provisional application No. 60/856,435, filed on Nov. 3, 2006.

(51) Int. Cl.
| | |
|---|---|
| *C07K 16/28* | (2006.01) |
| *A61K 35/28* | (2015.01) |
| *A61K 39/395* | (2006.01) |
| *C07K 16/32* | (2006.01) |
| *A61K 39/00* | (2006.01) |

(52) U.S. Cl.
CPC ......... *C07K 16/2896* (2013.01); *A61K 35/28* (2013.01); *A61K 39/3955* (2013.01); *C07K 16/2803* (2013.01); *C07K 16/2812* (2013.01); *C07K 16/2815* (2013.01); *C07K 16/2866* (2013.01); *C07K 16/32* (2013.01); *A61K 2039/505* (2013.01); *A61K 2039/54* (2013.01); *C07K 2317/73* (2013.01); *C07K 2317/76* (2013.01)

(58) Field of Classification Search
None
See application file for complete search history.

(56) References Cited

U.S. PATENT DOCUMENTS

2003/0099621 A1 5/2003 Chow et al.

FOREIGN PATENT DOCUMENTS

| EP | 1263463 | 12/2002 |
|---|---|---|
| WO | WO2004/002425 | 1/2001 |

OTHER PUBLICATIONS

Biffi et al ( J of Clinical Investigation, 2004, v.113, pp. 1118-1129.*
DePalma et al (Nature Medicine, 2003, v.9 pp. 789-795.*
Ballas et al., (2002) Adult bone marrow stem cells for cell and gene therapies: implications for greater use, 38:20-28, Journal of Cellular Biochemistry Supplement.
Bartolovic et al., (2004) "Inhibitory effect of imatinib on normal progenitor cells in vitro" Blood, vol. 103, No. 2, The American Society of Hematology, Washington, D.C., pp. 523-529.
Burt et al., (1998)"Treatment of autoimmune disease by intense immunosuppressive conditioning and autologous hematopoietic stem cell transplantation", Blood, vol. 92(10), The American Society of Hematology, Washington, D.C., pp. 3505-3514.
Chatenoud et al. (2005) "Monoclonal Antibody-Based Strategies in Autoimmunity and Transplantation" *Methods Mol Med.* 109:297-328.
Chen et al., (2004)"Bystander destruction of hematopoietic progenitor and stem cells in a mouse model of infusion-induced bone marrow failure", Blood, 104(6), The American Society of Hematology, Washington, D.C., pp. 1671-1678.
Czechowicz et al., (2007) "Efficient transplantation via antibody-based clearance of hematopoietic stem cell niches." Science, vol. 318, No. 5854, AAAS, Washington, DC. pp. 1296-1299.
Davis et al. (1998) "Subcutaneous bioavailability of a Primatizedtm IgG1 Anti-Human CD4 monoclonal antibody is dose dependent in transgenic mice bearing human CD4" *Drug Deliv.* 5(2):95-100.
Gaspar et al., (2006) "Successful Reconstitution of Immunity in ADA-SCID by tem Cell Gene Therapy Following Cessation of PEG-ADA and Use of Mild Preconditioning", Molecular Therapy vol. 14(4), The American Society of Gene Therapy, Milwaukee, WI. pp. 505-513.
Ishikawa et al., (2002) "An assay for long-term engrafting human hemopoietic cells based on newborn NOD/SCID Beta 2-microglobulin-(null) mice", Experimental Hematology, 30(5), Elsevier, Amsterdam, Netherland, pp. 488-494.

(Continued)

*Primary Examiner* — Michail A Belyavskyi
(74) *Attorney, Agent, or Firm* — Pamela J. Sherwood; Bozicevic, Field & Francis LLP

(57) ABSTRACT

The present invention provides a clinically applicable method of stem cell transplantation that facilitates engraftment and reconstitutes immunocompetence of the recipient without requiring radiotherapy or chemotherapy, and without development of GVHD or graft rejection. Aspects of the present invention are based on the discovery that the depletion of the endogenous stem cell niche facilitates efficient engraftment of stem cells into that niche. In particular, the present invention combines the use of selective ablation of endogenous stem cells, in combination with the administration to the recipient of exogenous stem cells, resulting in efficient, long-term engraftment and tolerance.

20 Claims, 11 Drawing Sheets

(56) References Cited

OTHER PUBLICATIONS

Jacobsohn et al., (2004) "Reduced intensity haemopoietic stem-cell transplantation for treatment of non-malignant diseases in children", The Lancet, 364(9429), The Lancet, London, United Kingdom, pp. 156-162.

Kraft et al., (2004) "Effect and kinetics of depleting ACK-2 anti c-kit monoclonal antibody on hematopoiesis and hematopoietic progenitors and ability to condition for bone marrow transplantation" Blood, (ASH Annual Meeting Abstracts), vol. 104, No. 11, Abstract 4963, The American Society of Hematology, Washington, D.C. p. 322B.

Kraft et al., (2007) "196—Ability of Anti C-Kit Targeting Monoclonal Antibody Ack-2 to Target Hematopoietic Stem Cells, and Facilitate Engraftment of Human CD34+ Engraftment and Hematolymphoid Development In Immunodeficient Mice: A Novel Antibody Based Conditioning Strategy", Biology of Blood and Marrow Transplantation Poster Session I, 13(2):72, Elsevier, Amsterdam, Netherlands.

Kraft et al., (2006) "378—Adult human hematopoietic cells differentiate into mature T cells via a CD3-4+8-intermediate within the mouse thymic microenvironment; a new model system for the study of human thymocyte development further enhanced by anti-murine c-Kit mAB", Biology of Blood and Marrow Transplantation, Poster Session II, vol. 12, No. 2, Carden Jennings Publishing Co, Charlottesville, VA, p. 131.

Lambert et al. (2005) "Drug-conjugated monoclonal antibodies for the treatment of cancer", Elsevier Science, pp. 543-549.

2018) Notice of opposition to European patent EP2088864, "Selective Immunodepletion of Endogenous Stem Cell Niche for Engraftment", 36 pages. Including cited references D1-D8.

Petersen et al. (2007) "Alloreactivity as therapeutic principle in the treatment of hematologic malignancies" *Dan Med Bull.* 54(2): 112-39.

Quesenberry et al., (1998) "Stem cell homing: Rolling, crawling, and nesting", PNAS, vol. 95, National Academy of Sciences, Washington, D.C. pp. 15155-15157.

2019) Summons to attend Oral Proceedings to European patent EP2088864, "Selective Immunodepleting of Endogenous Stem Cell Niche for Engraftment", 13 pages.

Vose et al (2001) "Transplantation of highly purified CD34+ Thy-1+ hematopoietic stem cells in patients with recurrent indolent non-Hodgkin's lymphoma" Biology Blood and Marrow Transplant, V7, pp. 680-687.

* cited by examiner

FIG. 7A
FIG. 7B
FIG. 7C
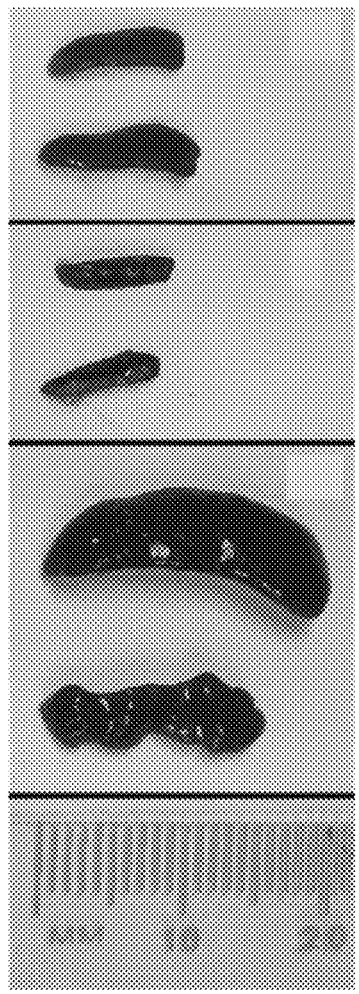
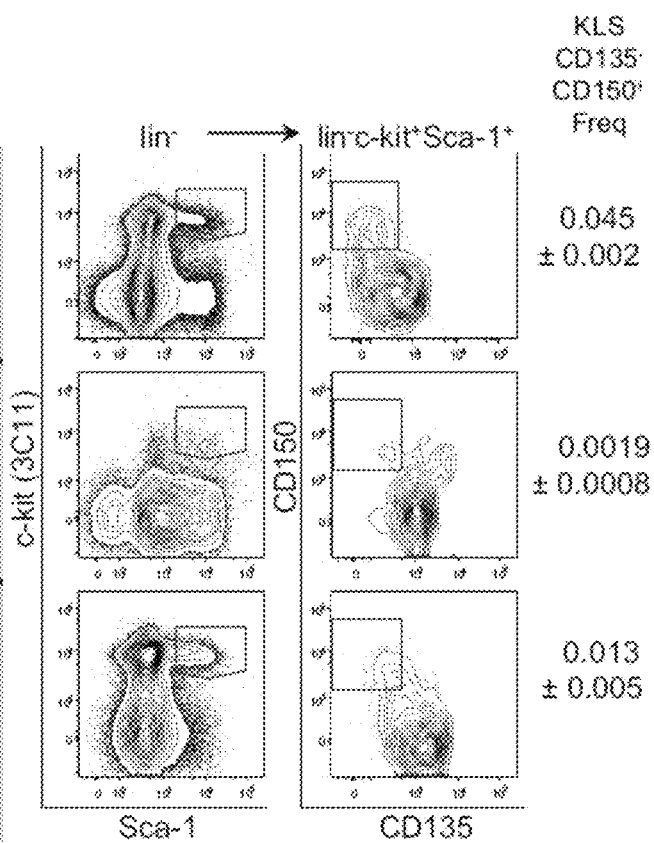

SELECTIVE IMMUNODEPLETION OF ENDOGENOUS STEM CELL NICHE FOR ENGRAFTMENT

CROSS REFERENCE

This application claims benefit and is a Continuation of application Ser. No. 16/035,187, filed Jul. 13, 2018, which claims benefit of Ser. No. 15/211,679 filed Jul. 15, 2016, now issued as U.S. Pat. No. 10,072,091, which claims benefit of Application of Ser. No. 12/447,634 filed Apr. 14, 2010, which is a 371 application and claims the benefit of PCT Application No. PCT/US2007/083529, filed Nov. 2, 2007, which claims benefit of U.S. Provisional Patent Application No. 60/856,435, filed Nov. 3, 2006, which applications are incorporated herein by reference in their entirety.

FEDERALLY SPONSORED RESEARCH AND DEVELOPMENT

This invention was made with Government support under contracts HL076335, HL058770, CA086065, DK078318 and A1007290 awarded by the National Institutes of Health. The Government has certain rights in the invention.

Stem cells provide the means for organisms to maintain and repair certain tissues, through the ability of these cells to self-renew and, through asymmetric replication, to generate differentiated cells. The potency of stem cells varies: whereas embryonic stem cells can give rise to all tissues of an organism, somatic stem cells may be limited to a specific lineage. Clinically, bone marrow and hematopoietic stem cell transplantation are widely used as a means of providing patients with the capacity to generate blood cells, usually where the patient has been depleted of endogenous stem cells by high dose chemotherapy or radiation. Bone marrow and peripheral blood are currently used as sources of autologous stem cells. In the future, cultured stem cells may provide an alternative to autologous cells for transplants.

In cancer patients, hematopoietic stem cells may be administered as supportive care to circumvent the morbidity and mortality associated with high-dose ablative treatment regimens that are used in attempts to effect a cure or prolonged survival in patients at high risk for treatment failure or recurrent cancer using conventional therapy.

Graft failure is defined as the failure to establish engraftment (primary graft failure) or loss of an established graft (secondary graft failure). Engraftment, (or graft failure) may be detected by determining the presence of donor-type cell surface antigens, isoenzymes, chromosome markers, or DNA-restriction fragment length polymorphisms. For hematopoietic engraftment, failure may be defined as granulocytes failing to recover to $>0.5\times10^9$/L or falling below this level for 3 days after initial recovery.

Graft failure or poor graft function may be caused by administration of myelosuppressive drugs, graft-versus-host disease, and infections in the early post transplant period. Ganciclovir, given for prevention or treatment of cytomegalovirus infections, is the most common drug producing graft failure; this is generally reversible when the drug is discontinued. Trimethoprim-sulfamethoxazole given to prevent *Pneumocystis carinii* infections is modestly myelosuppressive and only rarely produces graft failure. Cytomegalovirus, parvovirus, human herpesvirus 6, and mycobacterial and fungal infections may also compromise the graft. Poor engraftment may also result from microenvironment or marrow stroma dysfunction related to the patient's underlying disease or prior therapy.

Endogenous hematopoietic stem cells usually reside within BM sinusoids, although small numbers circulate in the peripheral blood. Mobilization into the peripheral blood is enhanced by the administration of cytokines such as granulocyte-colony stimulating factor (G-CSF) or granulocyte-macrophage-colony stimulating factor (GM-CSF). This mobilization results in a substantial rise in the number of circulating progenitor cells.

The interaction of stem cells with their microenvironment provides important cues for maintenance, proliferation and differentiation. This physical environment in which stem cells reside may be referred to as the stem cell microenvironment, or niche. The stromal and other cells involved in this niche provide soluble and bound factors, which have a multitude of effects. For example, two protein families, the TGFβ family and Wnt family, are known to be involved in stem cell regulation, and have been found to be operative in a number of systems and different organisms.

Cell-cell and cell to extracellular matrix (ECM) interactions are important for both the induction and maintenance of differentiation in several cell lineages. In the case of the ECM, specific cell surface receptors can bind to particular components of the ECM, activating an intracellular signal transduction pathway that is analogous to the signaling pathways that have been identified for polypeptide growth factors and growth inhibitors.

Adhesion to the extracellular matrix is mediated by several classes of receptor, the most extensively characterized being integrins. High expression of β1 integrins is required for maintenance of epidermal stem cells, and β1 integrins regulate differentiation of keratinocytes and other cell types through MAP kinase signaling. Integrins can maintain the position of cells in a tissue, and loss or alteration of integrin expression can lead to loss of a position in a niche. The extracellular matrix may also sequester and modulate the local concentration of secreted factors available within the stem cell niche.

Other signals that control stem cells require direct cell-cell contact. For example, interaction between the receptor Notch and its ligand Delta, both of which are transmembrane molecules, requires cell to cell contact. Notch signaling is involved in regulation of embryonic and adult tissues of vertebrates; examples include retinal neuroepithelium, skeletal muscle, and blood.

Various models have been proposed for the interaction between stem cell and niche. In its simplest form, a model has been suggested where, when a stem cell divides, only one daughter remains in the niche and the other daughter cell leaves the niche to differentiate. Alternatively, is has been suggested that engraftment phenotype is determined simply by the ratio of host to donor stem cell, and depletion of endogenous stem cells is unnecessary (Quesenberry and Becker (1998)).

Improved methods for engraftment of stem cells, including hematopoietic stem cells, are of great clinical interest. The present invention addresses this need.

SUMMARY OF THE INVENTION

Methods are provided for the engraftment of stem cells, e.g. hematopoietic stem cells, where endogenous stem cells are selectively ablated, thereby opening a niche for the engraftment of donor stem cells. Selective ablation substantially eliminates endogenous stem cells in the targeted tissue, without general ablation of cells in the tissue. The efficiency of engraftment is significantly enhanced by selective ablation, as compared to engraftment obtained without pretreatment. Such selective ablation allows improved function of the targeted tissue during the engraftment period, compared to methods involving non-selective ablation. The methods of the invention thus allow effective stem cell engraftment in the absence of non-selective ablation methods, e.g. radiation or chemotherapy, which have the undesirable effect of ablating differentiated cells involved in the function of the targeted tissue as well as undesirable side effects upon other tissues (e.g. on cells of the gastrointestinal system, hair growth), as well as increasing risk of secondary malignancies.

In one embodiment of the invention, selective ablation is accomplished by administering a stem cell specific, cytotoxic agent to the patient prior to engraftment. Following ablation, and after a period of time sufficient to substantially eliminate the stem cell ablative agent from the patient circulation, an effective dose of donor stem cells are introduced to the patient. Agents of interest include antibodies that specifically bind to markers selectively expressed on stem cells, e.g. hematopoietic stem cells.

In another embodiment, selective ablation is accomplished by administering an agent that selectively interferes with growth factor signaling essential for stem cell growth or maintenance, e.g. an agent that interferes with c-kit mediated signaling, thrombopoietin signaling, nerve growth factor signaling, etc. Such agents include, without limitation, antibodies that interfere with stem cell growth factor signaling; and drugs that inhibit stem cell growth factor signaling, e.g. imatinib, nilotinib, etc. Such agents are known in the art, or may be identified by screening candidate antibodies, etc. for inhibition of growth of the targeted stem cell, e.g. in an in vitro assay.

In one embodiment of the invention, the stem cells are hematopoietic stem cells. Such stem cells find use in the treatment of a variety of blood disorders, e.g. genetic disorders including aplastic anemia; sickle cell disease; thalassemias; severe immunodeficiency; and the like. In one embodiment of the invention, a method is provided for treating a genetic blood disorder in a patient, comprising administering to a patient a therapeutically effective amount of an agent, for example an antibody, that selectively ablates endogenous hematopoietic stem cells; and administering to the patient a therapeutically effective amount of hematopoietic stem cells from a donor.

The methods of the invention are also useful in the induction of tolerance in a patient, for example tolerance to donor tissue, e.g. in organ transplants; tolerance to autoantigens, e.g. in the context of treatment of autoimmune disease; and the like. In one embodiment of the invention, a method is provided for inducing tolerance in a patient, comprising administering to a patient a therapeutically effective amount of an agent, for example an antibody, that selectively ablates endogenous hematopoietic stem cells; and administering to the patient a therapeutically effective amount of hematopoietic stem cells from a donor, which administering may be performed in conjunction with introducing an allograft into said patient, treating autoimmune disease, etc.

BRIEF DESCRIPTION OF THE FIGURES

(FIG. 2A) ACK2 is cleared from serum of RAG2$^{-/-}$γc$^{-/-}$ mice seven days after injection. Serum of mice receiving 500 μg ACK2 was analyzed every two days for persistence of the ACK2 antibody by staining c-kit$^+$ mast cells. (FIG. 2B) ACK2 administration leads to depletion of BM HSCs. The number of KLS CD135$^-$ CD150$^+$ HSCs in both femurs and tibia of ACK2-treated and control mice was determined by flow cytometry at several timepoints after treatment. Mean values +/−SEM are shown (n=3 for each time point);  indicates p-value<0.001. (FIG. 2C) ACK2, but not 2B8 treatment, depletes functional HSCs from BM. Transplantation of 200,000 unfractionated bone marrow cells from mice treated with 500 μg ACK2 nine days earlier into irradiated recipients leads to decreased chimerism as compared to controls and another c-kit antibody, 2B8. Mean values +/−SEM are shown (n=5-8);  indicates p value<0.01. (FIG. 2D) ACK2 treatment does not directly cause HSC mobilization to the spleen. Single-cell suspensions of the spleens were generated from mice treated with 500 μg ACK2 nine days earlier and the entire suspensions were transplanted alongside 200,000 competitor bone marrow cells from wild type mice. Mean values +/−SEM are shown (n=3-9);  indicates p-value<0.001. (FIG. 2E) ACK2 inhibits SCF mediated HSC 19 proliferation. HSC were isolated from wild type mice and cultured in the presence of SCF or TPO and ACK2 or 2B8. Proliferation was observed by light microscopy.  indicates p-value<0.05 as compared to ACK2 treated samples. (FIG. 2F) ACK2 treatment selectively depletes HSCs at early timepoints. Total numbers of HSCs (lin$^-$c-kit$^+$Sca-1$^+$CD135$^-$CD150$^+$), MEPs (lin-c$^-$kit$^+$Sca-1-CD34$^-$FcγR$^-$), CMPs (lin$^-$c-kit$^+$Sca-1$^-$ CD34$^{low}$FcγR$^{low}$), and GMPs (lin$^-$c-kit$^+$Sca-1$^+$CD34$^{high}$FcγR$^{high}$) were quantified and compared to untreated control mice. Mean values +/−SEM are shown (n=3); ** indicates p-value<0.001 as compared to the relative number of HSCs at the same time point.

(FIG. 3A) ACK2 conditioning leads to higher donor myeloid chimerism. Donor granulocyte chimerism was measured following transplantation of 5000 HSCs in RAG2$^{-/-}$ mice conditioned with ACK2 seven days prior to transplant and compared to that of unconditioned mice. Mean values +/−SEM are shown (n=4);  indicates p-value<0.01. (FIG. 3B) HSC transplantation of ACK2-treated animals leads to lymphocyte reconstitution. Splenic donor-derived B and T-cells from ACK2-treated and unconditioned RAG2$^{-/-}$ mice were enumerated 39 weeks after transplantation with wild type HSCs. Mean values +/−SEM are shown (n=3-5);  indicates p-value<0.01. (FIG. 3C) Granulocyte chimerism accurately measures BM HSC chimerism. Peripheral blood granulocyte (Ter119$^-$CD3$^-$B220$^-$Mac-1$^{high}$ side scatter$^{high}$) chimerism at 37 weeks post-transplantation was correlated with HSC (c-kit$^+$ lineage$^-$ Sca-1$^+$ CD34$^-$CD150$^+$) chimerism in the BM at 39 weeks post-transplantation upon sacrifice. Solid line illustrates linear regression with 95% confidence interval shaded in gray. Dashed line represents theoretical values if donor granulocyte chimerism were identical to donor HSC chimerism. (FIG. 3D) Secondarily transplanted donor HSCs from ACK2 treated give rise to long term multilineage engraftment. Peripheral blood chimerism of B cells (B), T cells (T), and granulocytes (G) are shown 16 weeks post-secondary 20 transplant for 2 independent experiments. Mean values +/−SEM are shown (n=7-8 in each experiment).

(FIG. 4A) ACK2 treatment increases available HSC niche space. In two separate experiments, RAG2$^{-/-}$γc$^{-/-}$ mice were treated with ACK2 and transplanted nine days later with varying doses of HSCs (CD45.1). Donor granulocyte chimerism was measured as above 24 weeks after transplantation for the first experiment, and 4 weeks for the second experiment. Mean values +/−SEM are shown. (FIG. 4B) Flow cytometry profiles of mice transplanted with 35,000 HSCs. Chimerism of CD3$^-$B220$^-$Mac1$^{high}$ side scatter$^{high}$ peripheral blood granulocytes is shown.

FIG. 7A-7C. ACK2 treatment results in near complete yet transient HSC depletion in vivo. Bone marrow cellularity and HSC frequency were used to determine the number of HSCs in the bone marrow. Spleen sizes were also assessed for signs of extramedullary hematopoiesis. (FIG. 7A) control, (FIG. 7B) At time of ACK2 clearance (Day 9), (FIG. 7C) One week post ACK2 clearance (Day 16). Flow cytometric profiles of HSCs in lineage− BM using 3C11, a c-kit-specific antibody that binds a distinct epitope from ACK2, as well as KLS CD135$^-$CD150$^+$ frequency, of which 19.5% are HSCs, are shown adjacent to each corresponding time point. Mean values +/−SEM are shown (n=3 for each time point).

DETAILED DESCRIPTION OF THE EMBODIMENTS

Figure 1:
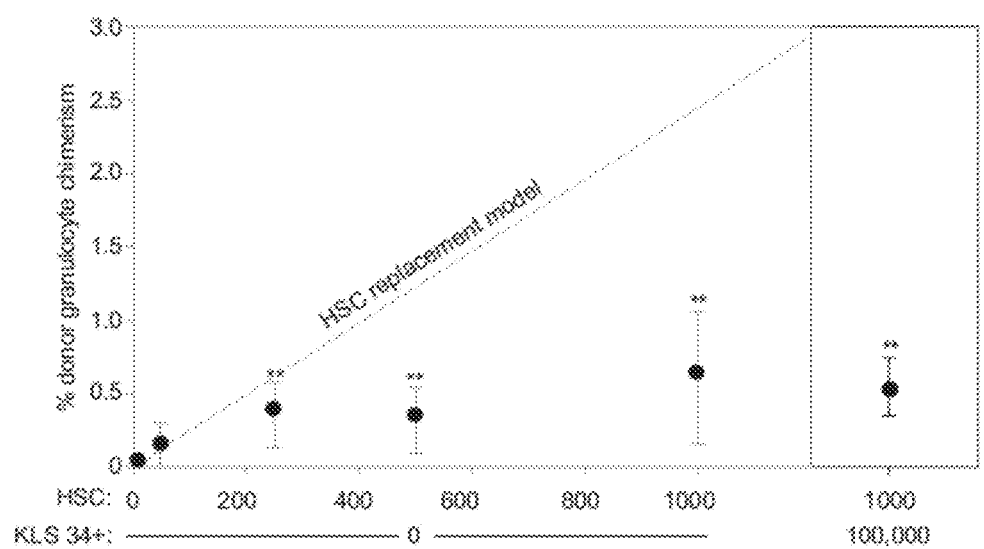
FIG. 1. Available HSC niches can be saturated with donor HSCs. Peripheral blood of transplanted unconditioned RAG2$^{-/-}$γc$^{-/-}$ mice was analyzed 16 weeks after HSC transplantation for GFP+ donor-derived Ter119$^-$CD3$^-$B220$^-$Mac-1$^{high}$ side scatter high granulocytes. In the right panel, mice were co-transplanted with CD45.1 1000 HSCs and 100,000 GFP$^+$ KLS CD34$^+$ cells. Mean values +/−SEM are shown (n=4-5 for each dose); ** indicates p-value<0.05 relative to the chimerism arising from the 10 HSC transplanted group. The dashed line represents the theoretical HSC chimerism if engraftment were to increase linearly with transplanted cell dose.

Methods are provided for the engraftment of stem cells, where endogenous stem cells are selectively ablated. Selective ablation may be accomplished by administering stem cell specific, cytotoxic antibodies to the patient prior to engraftment. Alternatively, selective ablation is achieved by administering an antibody or drug that selectively interferes with growth factor signaling essential for stem cell growth or maintenance, e.g. an agent that interferes with c-kit signaling, etc. Following ablation, and after a period of time sufficient to substantially eliminate the stem cell ablative agent from the patient circulation, exogenous stem cells are introduced to the patient, where the exogenous stem cells occupy the same niche as the ablated endogenous stem cells. Exogenous stem cells may be autologous, allogeneic, or xenogeneic relative to the patient.

The period of time required for clearance of the ablative agent may be empirically determined, or may be based on prior experience of the pharmacokinetics of the agent. Where the agent is an antibody, determination can be conveniently monitored by containing stem cells with recipient serum, and determining the presence of antibodies that bind to the stem cells. Alternatively, patient serum may be monitored for the presence of stem cell selective growth inhibition. The time for clearance is usually the time sufficient for the level of ablative agent to decrease as least about 10-fold from peak levels, usually at least about 100-fold, 1000-fold, 10,000-fold, or more. It is preferable to introduce the donor stem cells within the empty niche "window" following ablation, usually within about 3 days, about 2 days, about 1 day, or at the time of clearance.

It is an objective of the present invention to provide a new clinically applicable method of stem cell transplantation which facilitates engraftment and reconstitutes immunocompetence of the recipient without requiring radiotherapy or chemotherapy, or development of GVHD or graft rejection. Aspects of the present invention are based on the discovery that the depletion of the endogenous stem cell niche facilitates efficient engraftment of hematopoietic stem cells (HSCs). In particular, the present invention combines the use of selective ablation of endogenous stem cells, in combination with the administration to the recipient of exogenous stem cells, resulting in efficient, long-term engraftment and tolerance.

Endogenous stem cells are specifically ablated by administration of a selective agent, e.g. an antibody that kills the targeted cells, i.e. cells to which the agent binds; or a drug that selectively interferes with growth factor signaling required for stem cell growth or maintenance. In some embodiments, the agent is an antibody that selectively binds to the endogenous stem cells of interest. It will be understood by one of skill in the art that markers may be shared between stem cells, and thus a selective marker may bind to certain other cells present in the targeted tissue; and a selective drug may act on certain other cells. By ablation is meant a reduction in the number of viable endogenous stem cells in the targeted tissue, which may be a reduction of at least about 20% of viable endogenous stem cells, at least about 50%, at least about 75%, at least about 90% or more, by administration of one or more cytotoxic agents that selectively ablate said endogenous stem cells.

The targeted tissue is determined by the niche in which a stem cell of interest normally resides. In an adult mammal, endogenous hematopoietic stem cells reside in the bone marrow, and thus ablative agents will reduce the numbers of hematopoietic stem cells resident in bone marrow. In an adult mammal, neural stem cells may be resident in the hippocampus, and thus ablative agents will reduce the number of neural stem cells resident in the hippocampus. Mesenchymal stem cells are also resident in the bone marrow, and thus may be depleted, with agents for the appropriate markers, from bone marrow. One of skill in the art will readily determine the appropriate tissue for resident stem cells.

Exemplary markers for antibody mediated ablation of human hematopoietic stem cells include CD34; CD90 (thy-1); CD59; CD110 (c-mpl); c-kit; etc. Mouse hematopoietic stem cells may be selectively ablated through the markers Sca-1; CD150; c-kit; ESAM; etc. Markers useful for the ablation of mesodermal stem cells include FcγRII, FcγRIII, Thy-1, CD44, VLA-4a, LFA-1p, HSA, ICAM-1, CD45, Aa4.1, Sca-1, etc. Neural crest stem cells may be positively selected with antibodies specific for low-affinity nerve growth factor receptor (LNGFR). Neural stem/progenitor cells have been described in the art, and their use in a variety of therapeutic protocols has been widely discussed. For example, inter alia, U.S. Pat. No. 6,638,501, Bjornson et al.; U.S. Pat. No. 6,541,255, Snyder et al.; U.S. Pat. No. 6,498, 018, Carpenter; U.S. Patent Application 20020012903, Goldman et al.; Palmer et al. (2001) Nature 411(6833):42-3; Palmer et al. (1997) Mol Cell Neurosci. 8(6):389-404; Svendsen et al. (1997) Exp. Neurol. 148(1):135-46 and Shihabuddin (1999) Mol Med Today. 5(11):474-80; each herein specifically incorporated by reference. Human mesenchymal stem cells may be ablated using the markers such as SH2 (CD105), SH3 and SH4 and Stro-1.

In one embodiment of the invention, the marker for antibody mediated ablation is c-kit (CD117). Antibodies of interest may bind to, and block the signaling activity of, c-kit.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies for endogenous stem cell ablation may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies. The cross-linking of Fc receptors signals the effector cells to kill the target cells by cytolysis or apoptosis. In one embodiment, the induction is achieved via antibody-dependent cellular cytotoxicity (ADCC). In alternative embodiments, the antibodies are active in growth inhibition of the targeted cells, an ablation is achieved by interfering with growth factor signaling, e.g. antibodies specific for growth factor receptors such as c-kit.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

The selectivity of a particular antibody is typically determined by the ability of one antibody to competitively inhibit binding of the second antibody to the antigen, or by the ability of an antibody to cross-react with multiple epitopes. Any of a number of competitive binding assays can be used to measure competition between two antibodies to the same antigen, or between two antigens to one antibody. An exemplary assay is a BIACORE™ assay. Briefly in these assays, binding sites can be mapped in structural terms by testing the ability of interactants, e.g. different antibodies, to inhibit the binding of another. Injecting two consecutive antibody or antigen samples in sufficient concentration can identify pairs of competing antibodies for the same binding epitope. The antibody samples should have the potential to reach a significant saturation with each injection. The net binding of the second antibody injection is indicative for binding epitope analysis. Two response levels can be used to describe the boundaries of perfect competition versus non-competing binding due to distinct epitopes. The relative amount of binding response of the second antibody injection relative to the binding of identical and distinct binding epitopes determines the degree of epitope overlap.

Antibodies of interest for ablation may be tested for their ability to induce ADCC (antibody-dependent cellular cytotoxicity). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.). Preferably, the antibodies of the present invention induce at least 10%, 20%, 30%, 40%, 50%, 60%, or 80% cytotoxicity of the target cells.

Antibodies lacking fucose have been correlated with enhanced ADCC (antibody-dependent cellular cytotoxicity) activity, especially at low doses of antibody. Methods of preparing fucose-less antibodies include growth in rat myeloma YB2/0 cells (ATCC CRL 1662). YB2/0 cells express low levels of FUT8 mRNA, which encodes an enzyme (a 1,6-fucosyltransferase) necessary for fucosylation of polypeptides. Alternative embodiments for promoting cytotoxicity of cells with antibody treatment include antibody-mediated stimulation of signaling cascades resulting in cell death to the antibody bound cell. In addition antibody-mediated stimulation of the innate immune system (e.g. through NK cells) may also result in the death of tumor cells or virally-infected cells.

In some embodiments, the antibody is conjugated to an effector moiety. The effector moiety can be any number of molecules, including labeling moieties such as radioactive labels or fluorescent labels, or can be a cytotoxic moiety. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin-E and the like. Cytotoxic agents also include radiochemicals made by conjugating radioisotopes to antibodies. Targeting the cytotoxic moiety to transmembrane proteins serves to increase the local concentration of the cytotoxic moiety in the targeted area.

In some embodiments of the invention, the antibody is of an isotype that can bind Fc receptors on macrophages and drive opsonization (Rashid et al., J. Immunol 1992, 148:1382-1388). In some embodiments, the antibody is of an IgG isotype, e.g. IgG1, IgG2, IgG3, IgG4, etc. In some embodiments, the antibody is a rodent antibody of the IgG2b type. In other embodiments, the isotype is a human or humanized antibody of the IgG3 isotype (for review, see Davies and Metzger, Ann Rev Immunol 1983 1:87-117). Where a candidate antibody is of an isotype that does not bind Fc receptors and/or drive opsonization, the antibody may be modified through various methods known in the art to change the isotype to one that does bind Fc receptors and/or drive opsonization.

In certain embodiments, the ablative agent is a selective inhibitor of growth factor signaling required for stem cell maintenance or growth. Exemplary of such agents are those that inhibit c-kit mediated signaling, which is required for maintenance of hematopoietic stem cells. Such agents include antibodies that bind to and interfere with c-kit signaling; and drugs that selectively inhibit c-kit signaling, e.g. imatinib, nilotinib, certain 5-substituted 1,4-dihydroindeno[1,2-c]pyrazoles, etc., as known in the art and discussed in, for example, WO03028711; WO/2005/115304; Bioorganic & Medicinal Chemistry Letters (2007) 17:3136-3140; and Chow et al. (2007) Leuk Lymphoma. 2007 48(7):1379-88; each herein specifically incorporated by reference. Such agents may be screened for ablative activity in vitro or in vivo, e.g. as demonstrated in Example 1. Such screening methods may involve adding a candidate agent to a stem cell culture, and determining the growth inhibition achieved thereby. Selective inhibition may be determined by quantitating the growth in the presence of one or more growth factors. In addition to c-kit, growth factor receptors of interest include thrombopoietin receptor (CD110) on hematopoietic stem cells; and low-affinity nerve growth factor receptor (LNGFR) on neural stem cells. As with ablative antibodies, growth factor inhibitory agents are administered at a dose effective to decrease the number of viable endogenous stem cells in the targeted tissue, which may be a reduction of at least about 20% of viable endogenous stem cells, at least about 50%, at least about 75%, at least about 90% or more. For example, imatinib may be administered at a dose of from about 10 to about 500 mg/kg body weight. In some embodiments of the invention, a combination of ablative antibodies and growth factor inhibitory agents are administered. In such combination therapies, synergistic effects may be obtained where a decreased amount of one or both agents is utilized to achieve the desired effect.

For ablation, the ablative agent is formulated in a pharmaceutical composition. The exact dose will depend on the purpose of the treatment, and will be ascertainable by one skilled in the art using known techniques (e.g., Ansel et al., Pharmaceutical Dosage Forms and Drug Delivery; Lieberman, Pharmaceutical Dosage Forms (vols. 1-3, 1992), Dekker, ISBN 0824770846, 082476918X, 0824712692, 0824716981; Lloyd, The Art, Science and Technology of Pharmaceutical Compounding (1999); and Pickar, Dosage Calculations (1999)). As is known in the art, adjustments for patient condition, systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The administration of the agents can be done in a variety of ways as discussed above, including, but not limited to, orally, subcutaneously, intravenously, intranasally, transdermally, intraperitoneally, intramuscularly, intrapulmonary, vaginally, rectally, or intraocularly.

In one embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly useful are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art, e.g., Remington's Pharmaceutical Science and Goodman and Gillman, The Pharmacological Basis of Therapeutics, supra.

The compositions containing ablative agents, e.g. antibodies, can be administered for therapeutic treatment. Compositions are administered to a patient in an amount sufficient to substantially ablate targeted endogenous stem cells, as described above. An amount adequate to accomplish this is defined as a "therapeutically effective dose." Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

In an alternative embodiment of the invention, a conditioning agent, particularly an antibody specific for one or more of CD4; an NK cell specificity, a macrophage specificity, and CD8 is administered prior to infusion of exogenous stem cells. In one embodiment, the antibody specific for one or more of CD4; an NK cell specificity, a macrophage specificity, and CD8 is administered before cells are transplanted, usually from around 3 days to around 12 hours prior to transplantation, more usually around about 1 day prior to transplantation. A reduction in the level of T cells in the recipient animal may be maintained for at least one week, at least two weeks, at least 3 weeks, at least 4 weeks or more following the transplantation. Such a reduction may provide for around about a 50%, around about 75%, around about 90% decrease in CD4 positive T cells, compared to the T cell levels in the absence of treatment. Reduction of T cells may be accomplished, for example, by weekly administration of an anti-CD4 antibody, at a dose effective to decrease T cells by the desired level.

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages.

Endogenous stem cells may be characterized by both the presence of markers associated with specific epitopes identified by antibodies. Stem cells of interest include hematopoietic stem cells; neural crest stem cells (see Morrison et al. (1999) Cell 96:737-749); mesenchymal stem cells; mesodermal stem cells; etc. The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

For engraftment purposes, a composition comprising stem cells, including, without limitation, hematopoietic stem cells, is administered to a patient. Such methods are well known in the art. For example, Negrin et al. (2000) Biol Blood Marrow Transplant. 6(3):262-71 reports the transplantation of extensively purified, CD34$^+$Thy-1$^+$ peripheral blood hematopoietic stem cells. After high-dose chemotherapy, cells were infused at a median dose of 11.3×10$^5$/KG. Recipients had rapid and sustained hematopoietic engraftment. McNiece et al. (2000) Blood 96(9):3001-7 found that ex vivo expanded peripheral blood progenitor cells provide rapid neutrophil recovery after high-dose chemotherapy in patients with breast cancer. Autologous hematopoietic stem cell grafts are demonstrated by, inter alia, Balduzzi et al. (2001) Leukemia. 15(1):50-6. CD34$^+$ lineage$^-$ cells were infused, allowing prompt engraftment and immunological reconstitution. Abundant reports explore various methods for purification of stem cells and subsequent engraftment, including flow cytometry; an isolex system (Klein et al. (2001) Bone Marrow Transplant. 28(11):1023-9; Prince et al. (2002) Cytotherapy 4(2):137-45); immunomagnetic separation (Prince et al. (2002) Cytotherapy 4(2):147-55; Handgretinger et al. (2002) Bone Marrow Transplant. 29(9):731-6; Chou et al. (2005) Breast Cancer. 12(3):178-88); and the like. Each of these references is herein specifically incorporated by reference, particularly with respect to procedures, cell compositions and doses for hematopoietic stem cell transplantation.

The cells which are employed may be fresh, frozen, or have been subject to prior culture. They may be fetal, neonate, adult, etc. Hematopoietic stem cells may be obtained from fetal liver, bone marrow, blood, particularly G-CSF or GM-CSF mobilized peripheral blood, or any other conventional source. Cells for engraftment are optionally isolated from other cells, where the manner in which the stem cells are separated from other cells of the hematopoietic or other lineage is not critical to this invention. If desired, a substantially homogeneous population of stem or progenitor cells may be obtained by selective isolation of cells free of markers associated with differentiated cells, while displaying epitopic characteristics associated with the stem cells.

Cells may be genetically altered in order to introduce genes useful in the differentiated cell, e.g. repair of a genetic defect in an individual, selectable marker, etc., or genes useful in selection against undifferentiated ES cells. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is constitutive, pan-specific, specifically active in a differentiated cell type, etc. Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells (see Uchida et al. (1998) P.N.A.S. 95(20):11939-44).

Combinations of retroviruses and an appropriate packaging line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells.

The vectors may include genes that must later be removed, e.g. using a recombinase system such as Cre/Lox, or the cells that express them destroyed, e.g. by including genes that allow selective toxicity such as herpesvirus TK, bcl-xs, etc.

In the methods of the invention, the ablative agent and optional conditioning agent are administered as a short course of therapy prior to transplantation. Usually the ablative treatment is completed at least about one week prior to transplantation, at least about 5 days prior to transplantation, at least about 3 days prior to transplantation. The period of time between completion of ablative treatment and transplantation is sufficient to substantially eliminate ablative agents from the circulation of the patient. As used herein, the term "substantially eliminate" when referring to antibodies may provide for a concentration of less than about 10 ng/ml present in the bloodstream. Alternatively, a sample of patient blood or serum may be tested for in vitro cytotoxicity of exogenous stem cells, for example wherein not more than about 1% of the stem cells present in a sample are killed after exposure to said patient blood or serum sample.

Exogenous stem cells, which may be partially or substantially purified, are administered to the patient in accordance with standard practice, e.g. at a concentration of from about $10^4$ to about $10^6$ stem cells/kg patient weight.

Figure 10:
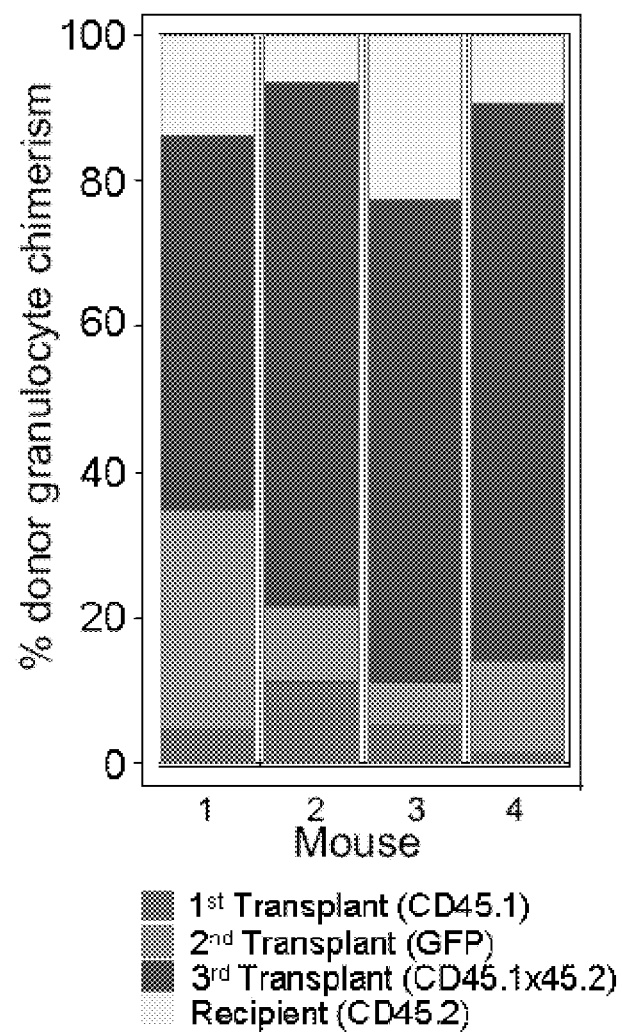
FIG. 10. Multiple rounds of ACK2 treatment and HSC transplantation result in consistently high levels of donor chimerism. A) RAG2$^{-/-}$γc$^{-/-}$ mice were conditioned with 500 μg of ACK2, and transplanted seven days later with CD45.1+5000 LT-HSCs. Mice were allowed to recover for seven days and were once again conditioned with ACK2 and transplanted seven days later with 5000 GFP$^+$ LT HSCs. A third round of ACK2 treatment and LT-HSC transplantation was performed using 5000 CD45.2+CD45.1+ HSCs. Peripheral blood was analyzed 24 weeks later for donor granulocyte chimerism as before. Chimerism values arising from each transplant in four separate animals are shown.

The process of ablation, optional conditioning and transplantation may be repeated, for example as shown in FIG. 10, in serial processes.

The embodiments of the system and methods according to the invention are clinically applicable to transplantation in human recipients and, for example, are adaptable to take into account such uncertainties as the timing of the availability of allogeneic cells for human recipients, and the like. Embodiments according to the invention are applicable to semi-allogeneic transplants such as, but not limited to, transplantation between related donor/recipients that are partially-mismatched at a major histocompatibility complex (MHC) class I or class II locus, and to fully-allogeneic transplants such as, but not limited to, transplantation between unrelated, fully mismatched MHC donor/recipient, including xenogeneic transplants to humans. In specific embodiments, transplants according to the invention are performed wherein the donor and recipient share no histocompatibility loci, for example, transplants between species, or transplants between donor and recipient of the same species wherein donor and recipient share no loci. In a more specific example, the transplant is from a human donor to a human recipient, where the donor and recipient share no HLA markers. The invention encompasses the transplantation from donors to recipients of any species, wherein the donor and recipient share no immunodeterminants analogous to HLA markers or MHC loci. In various embodiments, donor and recipient may be genetically unrelated individuals, or may be from the same immediate family.

Embodiments of the invention include transplantation into a patient suffering from a genetic blood disorder, where exogenous stem cells of a normal phenotype are transplanted into the patient. Such diseases include, without limitation, the treatment of anemias caused by defective hemoglobin synthesis (hemoglobinopathies).

The normal adult Hb molecule (Hb A) consists of two pairs of α and β polypeptide chains. Fetal Hb (Hb F, in which gamma chains replace beta chains) gradually decreases in the first months of life until it makes up <2% of total Hb in adults. In certain disorders of Hb synthesis and in aplastic and myeloproliferative states, Hb F may be increased. Normal blood also contains about 2.5% of Hb A2 (composed of alpha and delta chains). Defects may result in Hb molecules with abnormal physical or chemical properties; some result in anemias that are severe in homozygotes but mild in heterozygotes. Some patients may be heterozygous for two such abnormalities and have anemia with characteristics of both traits.

Sickle cell diseases include HbS Disease; drepanocytic anemia; meniscocytosis. Chronic hemolytic anemia occurring almost exclusively in blacks and characterized by sickle-shaped RBCs caused by homozygous inheritance of Hb S. Homozygotes have sickle cell anemia; heterozygotes are not anemic, but the sickling trait (sicklemia) can be demonstrated in vitro. In Hb S, valine is substituted for glutamic acid in the sixth amino acid of the beta chain. Deoxy-Hb S is much less soluble than deoxy-Hb A; it forms a semisolid gel of rodlike tactoids that cause RBCs to sickle at sites of low $PO_2$. Distorted, inflexible RBCs adhere to vascular endothelium and plug small arterioles and capillaries, which leads to occlusion and infarction. Because sickled RBCs are too fragile to withstand the mechanical trauma of circulation, hemolysis occurs after they enter the circulation. In homozygotes, clinical manifestations are caused by anemia and vaso-occlusive events resulting in tissue ischemia and infarction. Growth and development are impaired, and susceptibility to infection increases. Anemia is usually severe but varies highly among patients. Anemia may be exacerbated in children by acute sequestration of sickled cells in the spleen.

Aplastic crisis occurs when marrow erythropoiesis slows during acute infection (especially viral). Bone infarctions produce pain crisis, the most common symptom complex in Hb S-S, S-A, and S-C states. Long bone pain is the most common complaint; in children, severe pain in the hands and feet is common and typical. Arthralgia with fever may occur, and avascular necrosis of the femoral head is common. Chronic punched-out ulcers about the ankles are also common. Severe abdominal pain with vomiting may simulate severe abdominal disorders; such painful crises are usually associated with back and joint pain. Hemiplegia, cranial nerve palsies, and other neurologic disturbances may result from occlusion of major intracranial vessels. Infections, particularly pneumococcal, are common, especially in early childhood, and are associated with a high mortality rate.

At the present time, therapy is symptomatic because there is no effective in vivo anti-sickling drug. In general, crises are managed with vigorous oral or IV hydration and analgesics, including narcotics for pain. Transfusions may be given as needed (usually every 3 to 4 wk) to maintain the Hb A at >50% (50 to 70%) of the total Hb. Bone marrow transplantation has been successful in a small number of patients. Gene therapy currently offers the best hope for cure.

In hemoglobin C disease, the degree of anemia is variable but can be moderately severe. Of blacks in the USA, 2 to 3% show the trait. Symptoms in homozygotes are caused by anemia. Arthralgia is common. Abdominal pain may be present, but the abdominal crises of sickle cell anemia do not occur. The patient may be mildly jaundiced. The spleen is usually enlarged. Episodes of splenic sequestration with left upper quadrant pain and abrupt decreases in RBC values may occur; if they are severe, splenectomy may be required.

In homozygotes, anemia is normocytic, with 30 to 100% target cells, associated spherocytes, and, rarely, crystal-containing RBCs seen in the smear. In patients with microcytosis who do not have Fe deficiency, concomitant alpha-thalassemia is present. Reticulocytes are increased slightly, and nucleated RBCs may be present. The RBCs do not sickle. On electrophoresis, the Hb is type C. Serum bilirubin is slightly elevated, and urobilinogen is increased in the stool and urine. There is no specific treatment. Anemia is usually not severe enough to require blood transfusion.

Hemoglobin E disease is the third most prevalent Hb worldwide (after Hb A and Hb S), primarily in Southeast Asian (>15%) and black populations, but rarely in Chinese populations. Hb E is $\alpha_2 \beta_2$ 26 (glu→lys). In heterozygotes (Hb AE), no peripheral blood abnormalities are found. Homozygous Hb E is associated with a mild microcytic anemia with prominent targeting. Double heterozygotes for Hb E and beta-thalassemia have a hemolytic disease more severe than S-thalassemia.

Thalassemias are a group of chronic, inherited, microcytic anemias characterized by defective Hb synthesis and ineffective erythropoiesis, particularly common in persons of Mediterranean, African, and Southeast Asian ancestry. Thalassemia is among the most common inherited hemolytic disorders. It results from unbalanced Hb synthesis caused by decreased production of at least one globin polypeptide chain ($\beta$, $\alpha$, $\gamma$, $\delta$).

β-thalassemia results from decreased production of β-peptide chains. The disease is usually autosomal recessive: heterozygotes are carriers and have asymptomatic mild to moderate microcytic anemia (thalassemia minor); the typical symptoms occur in homozygotes (thalassemia major). Autosomal dominant forms also occur. α-Thalassemia, which results from decreased production of α-polypeptide chains, has a more complex inheritance pattern, because genetic control of α-chain synthesis involves two pairs of structural genes. Heterozygotes for a single gene defect (alpha-thalassemia-2 [silent]) are usually free of clinical abnormalities. Heterozygotes for a double gene defect or homozygotes for a single gene defect (alpha-thalassemia-1 [trait]) tend to manifest a clinical picture similar to heterozygotes for β-thalassemia. Inheritance of both a single gene defect and a double gene defect more severely impairs alpha-chain production. α-Chain deficiency results in the formation of tetramers of excess β chains (Hb H) or, in infancy, γ chains (Barts Hb). Homozygosity for the double-gene defect is lethal because Hb that lacks alpha chains does not transport $O_2$.

Clinical features of thalassemias are similar but vary in severity. β-Thalassemia minor is clinically asymptomatic. β-Thalassemia major (Cooley's anemia) presents with symptoms of severe anemia, markedly expanded marrow space, and transfusional and absorptive Fe overload. Patients are jaundiced, and leg ulcers and cholelithiasis occur (as in sickle cell anemia). Splenomegaly is common, and the spleen may be huge. If splenic sequestration develops, the survival time of transfused normal RBCs is shortened. Bone marrow hyperactivity causes thickening of the cranial bones and malar eminences. Long bone involvement makes pathologic fractures common. Growth rates are impaired, and puberty may be significantly delayed or absent. Fe deposits in heart muscle may cause dysfunction and heart failure. Hepatic siderosis is typical, leading to functional impairment and cirrhosis. α-Thalassemia-1 (trait) has a similar presentation to β-Thalassemia minor. Patients with Hb H disease often have symptomatic hemolytic anemia and splenomegaly.

Allogeneic bone marrow transplantation has been successful in the small numbers of patients who have received it, but transplantation for hematologic diseases have constrained by the morbidity and mortality associated with radiation and chemotherapy used for conditioning.

Aplastic anemia results from a loss of RBC precursors, either from a defect in stem cell pool or an injury to the microenvironment that supports the marrow, and often with borderline high MCV values. The term aplastic anemia commonly implies a panhypoplasia of the marrow with associated leukopenia and thrombocytopenia.

About ½ of the cases of true aplastic anemia are idiopathic. A rare form of aplastic anemia, Fanconi's anemi occurs in children with abnormal chromosomes. Pure RBC aplasia implies a mechanism selectively destructive to the erythroid precursors. Chronic RBC aplasia has been associated with hemolytic disorders (acute erythroblastopenia), thymomas, and immunologic injury and less often with drugs (e.g., tranquilizers, anticonvulsants), toxins (organic phosphates), riboflavin deficiency, and chronic lymphocytic leukemia. A rare congenital form, Blackfan-Diamond syndrome, originally believed to manifest during infancy, has been diagnosed in adulthood.

Bone marrow transplantation from an identical twin or an HLA-compatible sibling is a proven treatment for severe aplastic anemia, particularly in patients aged <30. At diagnosis, siblings may be evaluated for HLA compatibility.

Combined immunodeficiency is a group of disorders characterized by congenital and usually hereditary deficiency of both B- and T-cell systems, lymphoid aplasia, and thymic dysplasia. The combined immunodeficiencies include severe combined immunodeficiency, Swiss agammaglobulinemia, combined immunodeficiency with adenosine deaminase or nucleoside phosphorylase deficiency, and combined immunodeficiency with immunoglobulins (Nezelof syndrome). Most patients have an early onset of infection with thrush, pneumonia, and diarrhea. If left untreated, most die before age 2. Most patients have profound deficiency of B cells and immunoglobulin. The following are characteristic: lymphopenia, low or absent T-cell levels, poor proliferative response to mitogens, cutaneous anergy, an absent thymic shadow, and diminished lymphoid tissue. *Pneumocystis* pneumonia and other opportunistic infections are common.

Several variants of the disorder exist. In 67% of cases, X-linked or autosomal recessive inheritance can be established. Most of the patients with X-linked inheritance have X-linked severe combined immunodeficiency, associated with mutations of the γ chain of the IL-2 receptor.

About half of patients with an autosomal recessive inheritance have adenosine deaminase (ADA) deficiency, a purine salvage pathway enzyme that converts adenosine and deoxyadenosine to inosine and deoxyinosine, respectively. ADA deficiency results in elevated quantities of deoxyadenosine triphosphate (dATP), which inhibits DNA synthesis. ADA-deficient patients may be normal at birth but develop progressive immunologic impairment as dATP accumulates. In Nezelof syndrome (combined immunodeficiency with Igs), there is a profound cellular immunodeficiency but normal, near-normal, or elevated levels of Igs, but with poor antibody function.

Other variants include cytokine deficiencies (IL-1 deficiency, IL-2 deficiency, multiple cytokine deficiency), structural defects of the T-cell receptor, signal transduction defects, absence of HLA class II and/or class I antigens (bare lymphocyte syndrome), short-limbed dwarfism, cartilage hair hypoplasia with immunodeficiency, and combined immunodeficiency with eosinophilia (Omenn's syndrome).

EXPERIMENTAL

Example 1

Antibody-Based Depletion of Hematopoietic Stem Cells Empties Niches for Efficient Transplantation We demonstrate that administration of a depleting antibody specific for c-kit leads to the highly efficient removal of host hematopoietic stem cells (HSCs) and high levels of donor HSC chimerism following transplantation.

Upon intravenous transplantation, hematopoietic stem cells (HSCs) can home to specialized bone marrow niches, yet engraftment levels rarely exceed 0.5% following transplantation into immunodeficient recipients without toxic conditioning. Here, we provide evidence that, aside from immune barriers, donor HSC engraftment is restricted by occupancy of appropriate niches by host HSCs. Administration of ACK2, a depleting antibody specific for c-kit, led to the transient removal of >98% of endogenous HSCs and transplantation of these animals with donor HSCs led to chimerism levels of up to 90%. Extrapolation of these methods to humans may enable efficient yet mild conditioning regimens for transplantation.

HSCs are the only cells within the bone marrow (BM) that possess the ability to differentiate to all blood lineages and yet self-renew and maintain themselves for life. These two properties, coupled with the ability to home to highly specialized microenvironments within the bone marrow that enable them to function properly, have allowed HSCs, included within the hematopoietic preparations in BM transplants, to become the only stem cells in routine clinical use. They are widely used for the treatment of some hematological disorders, such as severe combined immunodeficiency (SCID), and hematopoietic failure following irradiation and chemotherapy. They are also used in a variety of other hematologic disorders. In animal models and anecdotally in humans, HSC from normal donors have also been implicated to be useful in the treatment of a wide range of autoimmune disorders such as diabetes, the NZB/W model of lupus, and multiple sclerosis. HSC are also capable of inducing transplantation tolerance to HSC donor tissues. However, the use of HSC for such disorders is not common due to the toxic conditioning regimens currently required for engraftment and the graft vs. host disease caused by T cells in the marrow or mobilized blood that supplies the HSC.

Typically, efficient allogeneic transplantation requires conditioning of the recipient with toxic, cytoreductive treatments in order to prevent immunological rejection of the graft. Nevertheless, even in the absence of immune barriers, the levels of donor engraftment following HSC transplantation appear to be restricted in unconditioned recipients. Consistent with clinical data regarding BM transplantation (BMT) of SCID patients that had not been conditioned with cytoreductive drugs, we found that HSC transplantation into unconditioned SCID mice led to a restoration of functional B and T lymphocytes, but donor HSC chimerism remained at <1%. These low levels of chimerism could also be achieved when CD45.1 HSCs were transplanted into unconditioned wild type CD45.1×CD45.2 mice, which are genetically incapable of rejecting the graft, but not CD45.2 recipients, which presumably can reject the graft on the basis of antigenic differences of the CD45 protein.

We hypothesized that donor HSC engraftment might be limited by the occupancy of appropriate HSC niches and that the specific removal of host HSCs from these niches might increase donor HSC engraftment. In the studies described below, we provide evidence that the specific antibody-mediated depletion of host HSCs leads to a dramatic improvement in the efficiency of donor HSC engraftment. These data confirm that niche availability regulates the efficiency of HSC transplantation. Moreover, these studies provide a framework for the use of highly specific antibodies to safely deplete and replace genetically abnormal HSCs for the treatment of hematological disorders.

We have shown previously that normal HSC in marrow engage in continuous recirculation from marrow to blood back to marrow. Cells in the blood enter the bone marrow, spleen, and liver and can establish long-term HSC self-renewal and hematopoiesis. We have previously demonstrated that at any instant about 0.1-4 0.5% of HSC are in this process, leading us to propose that there are equivalent numbers of empty HSC niches at any instant. Consistent with this hypothesis, we found little difference in granulocyte or HSC chimerism when cell doses ranging from 500-4000 purified HSCs were transplanted in a single bolus into either unconditioned recombinase activating gene 2-deficient (RAG2−/−) or RAG2−/− interleukin-2 common gamma chain-deficient (RAG2−/−γc−/−) mice, which behave similarly to each other with respect to HSC transplantation.

To more rigorously address whether appropriate niches in unconditioned recipients can be saturated by transplanted HSCs in a dose dependent manner, we transplanted unconditioned Rag2−/−γc−/− mice with varying numbers of c-kit$^+$ lineage$^-$Sca-1$^+$ (KLS) CD34$^-$CD150$^+$ HSCs from GFP-transgenic mice. Peripheral blood granulocyte chimerism was measured at 16 weeks post transplant, which we have previously shown to accurately reflect donor HSC chimerism in this unconditioned system. Donor granulocyte chimerism increased significantly in doses between 10 and 250 transplanted HSCs, but transplantation of more than 250 cells led to at most modest increases in chimerism (FIG. 1).

Thus, increasing the dose of transplanted HSCs did not result in a linear increase in donor chimerism as would be expected in a model where endogenous HSCs can be readily replaced by transplanted HSCs. Instead, the data confirm that the HSC niche is a highly specific entity, and suggest that the number of niches available for engraftment at any given point under homeostatic conditions are similar to the number of HSCs estimated to be in their circulatory phase. In this model, increased doses of transplanted HSCs lead to slightly increased chimerism levels by increasing the probability that an endogenous HSC exits into circulation and vacates a niche in close spatial proximity to an as yet non-engrafted donor HSC. However, the process is clearly inefficient and non-linear, since transplantation of 1000 HSCs, equivalent to approximately 5% of the total number of HSCs in a mouse, led only to 0.6% chimerism (FIG. 1).

To determine whether HSCs alone or other cell types as well can occupy these niches, we competitively transplanted unconditioned Rag2−/−γc−/− (CD45.2) mice with 1000 CD45.1 HSC along with 100,000 GFP KLS CD34+ progenitor cells, which are the immediate downstream progeny of HSCs. The inclusion of 100,000 KLS CD34$^+$ progenitor cells in the transplant did not affect the engraftment of the HSC, as there was no significant difference in donor chimerism relative to recipients that received 1000 HSCs alone (FIG. 1). Despite the inclusion of a 100-fold excess of progenitor cells, the donor chimerism resulting from the 1000 HSC was significantly higher than the 10 HSC cell dose (FIG. 1). These data imply that KLS CD34$^+$ progenitor cells do not effectively compete with HSCs for the same niches, and that the presence or absence of these non-self-renewing progenitor cells does not affect HSC engraftment.

GFP$^+$ donor-derived myeloid and lymphoid contribution from the transplanted KLS CD34$^+$ cells did persist through at least 8 weeks post-transplantation at levels similar to those we have observed previously, suggesting that HSCs and their immediate progeny use distinct niches to maintain function. Studies in unconditioned mice have demonstrated that unfractionated donor BM transplants lead to chimerism levels that are linearly proportional to the dose of transplanted cells, suggesting that "space" is not a limiting factor in BM transplants. However, these studies did not determine whether all cell types or only certain subsets of cells that are present within the heterogeneous BM compartment are readily displaced.

Figure 5:
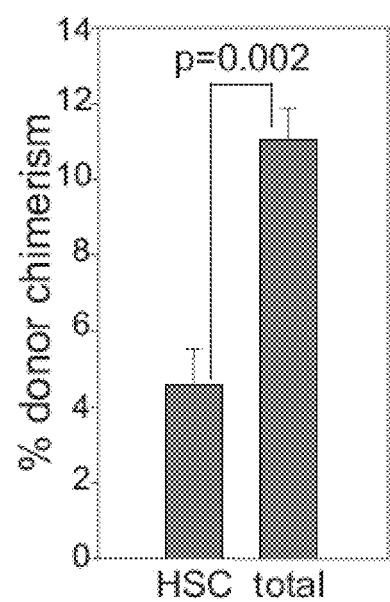
FIG. 5. Total donor chimerism does not accurately reflect HSC chimerism following unfractionated bone marrow transplantation. 6.5×10$^7$ unfractionated nucleated bone marrow cells from wild type female CD45.2 mice were transplanted into unirradiated wild type female CD45.1×CD45.2 F1 recipients. Total peripheral blood and BM HSC (defined as KLS CD135$^-$CD34$^-$) chimerism was measured 16 weeks after transplantation.

Because HSCs represent <0.01% of all nucleated bone marrow cells, we wished to determine whether the total donor chimerism measured in these studies accurately reflected HSC chimerism. To examine this issue, we transplanted $6.5 \times 10^7$ unfractionated bone marrow cells from female CD45.2 mice into female CD45.1×CD45.2 F1 recipients to exclude the possibility of graft rejection. This transplanted cell dose represents 12-15% of the total recipient bone marrow cellularity by one estimate, or 20-28% by another. Sixteen weeks after transplant, we measured the total peripheral blood chimerism and the bone marrow HSC chimerism directly. The total chimerism in the peripheral blood was 11% (FIG. 5), similar to the predictions made in earlier studies. However, the mean HSC chimerism was only 4.5%, approximately 2.5 fold lower than the total chimerism (FIG. 5). These data demonstrate that measurement of total chimerism leads to an overestimation of BM HSC chimerism. Thus, the data confirm that even in this system, HSC replacement is inefficient in unconditioned recipients.

Based on these data, we reasoned that the specific elimination of host HSCs that occupy these highly specific niches in unconditioned animals would allow for high levels of donor HSC engraftment. In vivo administration of antibodies specific for particular antigens, such as CD20, has been shown in many contexts to mediate specific cell depletion through opsonization, antibody-dependent cell-mediated cytotoxicity (ADCC), recruitment of complement, or the disruption of essential signaling pathways. We hypothesized that antibodies might also be used to target and deplete HSCs, thereby creating more available HSC niches for donor HSC engraftment. To test this hypothesis, we compared a number of different monoclonal antibodies and selected ACK2, an antibody known to recognize c-kit, the receptor for stem cell factor (SCF), and antagonize function in vivo.

Figure 2A:
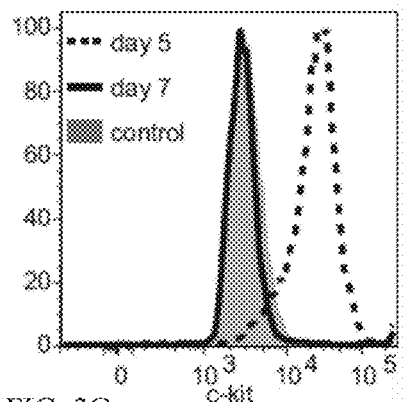
FIG. 2A-2F. ACK2 treatment depletes HSCs in vivo.

We further hypothesized that if the ACK2 antibody were capable of depleting endogenous HSCs, residual antibody in the serum of mice would also inhibit and/or deplete transplanted donor HSCs. To determine the kinetics of antibody clearance in vivo, we administered 500 μg of ACK2 intravenously to Rag2−/−γc−/− immunodeficient mice and tested the serum every two days for the presence of antibody by staining c-kit+ mast cells. Residual antibody was detected in the serum up to five days after injection; however all detectable ACK2 antibody was cleared from the serum by seven 7 days after injection (FIG. 2A). In certain other ACK2 preparations, antibody persisted in the serum of mice for up to eight days after injection.

Figure 2B:
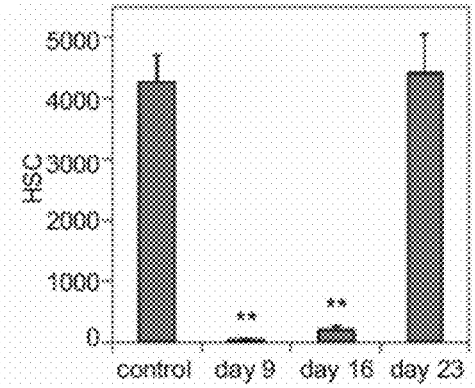

To determine whether ACK2 administration could deplete HSCs in vivo, we quantified HSC numbers and frequencies in the bone marrow of treated mice at the time of ACK2 clearance. At this time point, we observed a ~99% decrease in the number of phenotypically identifiable HSCs (KLS CD135−CD150+) (FIG. 2B). We also quantified the number of bone marrow HSCs using expression of Sca-1 and CD150, coupled with the lack of expression of CD34, CD135, CD244, CD48, and CD41 and other antigens associated with lineage commitment and observed a similar decrease in HSC numbers and frequency. This treatment did not lead to obvious HSC mobilization, since an increase in phenotypic HSCs was not detected in the spleens or blood of ACK2-treated mice.

Figure 2C:
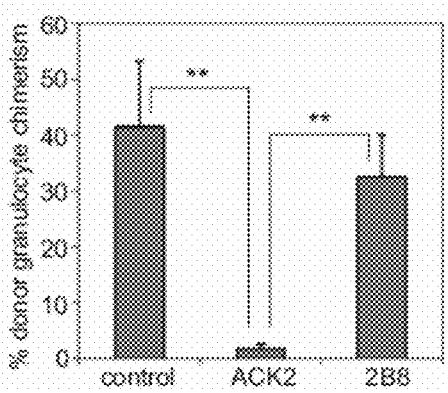

In order to control for the possibility that ACK2 treatment changed the cell surface phenotype of host HSCs and to verify that ACK2 depleted functional host HSCs, unfractionated bone marrow from ACK2-conditioned or rat IgG-treated control animals were transplanted into irradiated recipients alongside competitor marrow. Rag2$^{-/-}$γc$^{-/-}$ mice were conditioned with 500 μg ACK2, and at time of antibody clearance, 200,000 bone marrow cells from ACK2-conditioned animals were transplanted alongside 200,000 congenically marked competitor bone marrow cells from untreated wild type mice into lethally irradiated recipients. Transplantation of BM from ACK2-treated animals led to markedly reduced engraftment values relative to those obtained by transplantation of control BM (FIG. 2C). These data demonstrate that ACK2 depletes functional HSCs from the BM.

Figure 2D:
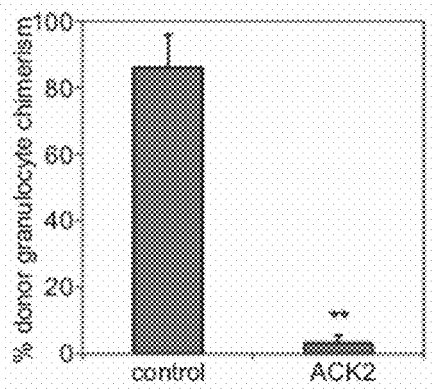

To determine the potential direct mobilizing effects of ACK2 treatment, the entire splenocyte population of ACK2-conditioned or control animals was transplanted alongside 200,000 congenically marked competitor bone marrow cells from untreated wild type mice into lethally irradiated recipients. The donor chimerism resulting from transplantation of splenocytes from ACK2-conditioned animals was significantly reduced relative to the chimerism resulting from transplantation of control splenocytes (FIG. 2D). These data indicate that ACK2-treatment depletes HSCs from the spleen as well as the BM, and does not directly induce early HSC mobilization.

Figure 2E:
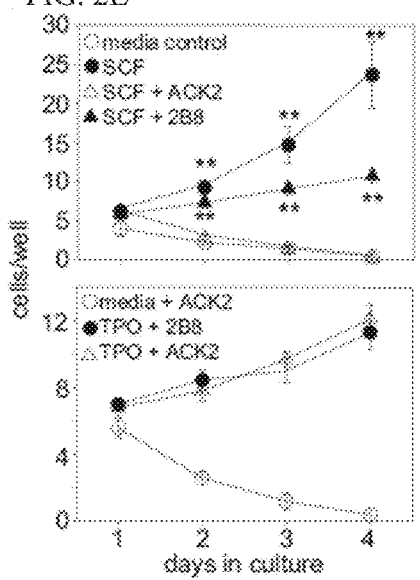

In order to determine the mechanism by which ACK2 depletes HSCs, the effects of ACK2 treatment were compared to that of 2B8, another c-kit monoclonal antibody of the same IgG2b isotype, which stains c-kit expressing cells with equivalent intensity as ACK2. However, 2B8 treatment did not decrease functional HSC numbers in vivo, and transplantation of bone marrow cells from mice treated with 2B8 resulted in normal engraftment (FIG. 2C). We hypothesized that ACK2 may deplete HSCs by antagonizing SCF-mediated c-kit function, as has been previously shown in melanocytes. To test this hypothesis, we cultured purified HSCs in the presence of ACK2 and found that it inhibited SCF dependent proliferation (FIG. 2E), but not thrombopoietin (TPO)-mediated proliferation (FIG. 2E). Unlike ACK2, the effects of 2B8 (a different anti-c-kit antibody) on SCF-mediated proliferation were modest (FIG. 2E). Therefore, it is likely that ACK2 causes HSC depletion through the inhibition of SCF signaling while 2B8 binds to a region of the c-kit molecule that is not essential for signaling. The importance of SCF-mediated c-kit signaling for HSCs has been demonstrated in W/W mice, which lack functional c-kit expression and die in utero unless transplanted with normal HSCs.

Figure 2F:
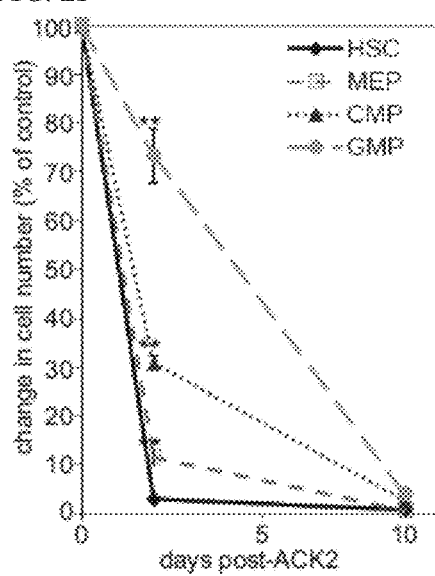

Additionally, we assayed the effect of ACK2 on a variety of hematopoietic progenitor cells in vivo at two and nine days after ACK2 administration. Two days post ACK2 administration, all myeloid progenitors in the bone marrow, which express similar levels of c-kit as do HSCs, began to decline, however HSC were most dramatically impacted (FIG. 2F). Thus, these data are again inconsistent with a direct Fc-mediated depleting activity of c-kit+ cells by ACK2 and rather support a mechanism by which progenitor cells are gradually lost either due to the lack of replenishment by HSCs and other early progenitors within the KLS compartment, or by blockade of their c-kit receptors.

Figure 6:
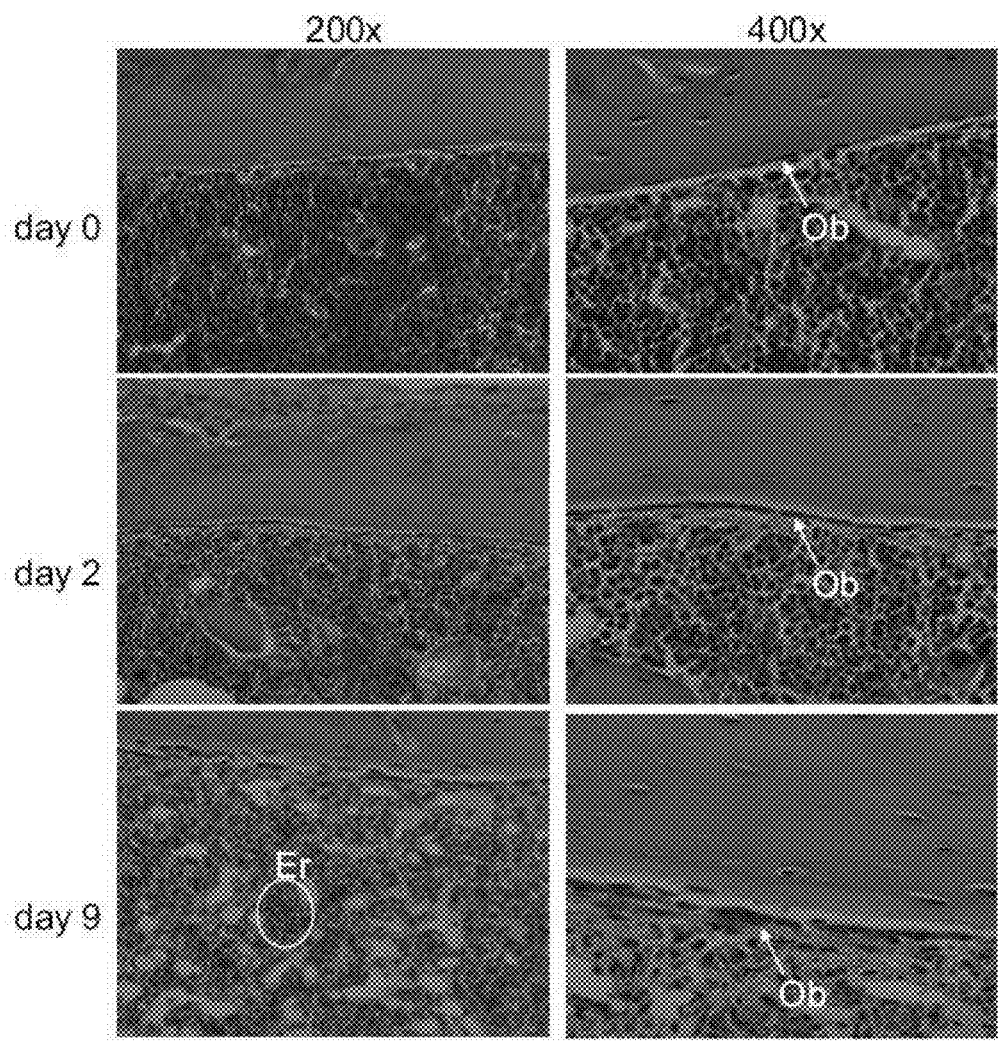
FIG. 6. ACK2 treatment leads to marked reduction of BM cellularity and increases in osteoblast size. Humerus bones from untreated (Day 0) or ACK2-treated RAG2-/-γc-/- mice were isolated 2 or 9 days after antibody injection. Bones were fixed, decalcified, paraffin embedded, and hematoxylin and eosin stains were performed on sections. Ob, osteoblast; Er, immature erythroid colony.

Consistent with this mechanism, by nine days post ACK2 administration, HSCs (FIG. 2F), myeloid progenitors (FIG. 2F), and common lymphoid progenitors were severely diminished. Upon histological examination, we found a similar gradual diminishment of bone marrow cellularity (FIG. 6). Additionally, we observed a progressive increase in the size of osteoblasts (FIG. 6, right column). These data indicate that ACK2 causes a significant but transient depletion of host HSCs and results in a short window in which ACK2-treated animals are receptive to donor HSC transplantation.

Importantly, all mice survived the treatment with no obvious signs of distress aside from a temporary loss of coat color, as previously reported. The lack of mortality in ACK2-treated mice is likely due to the mechanism of ACK2 depletion, in that mature effector blood cells are not directly affected by the treatment and are only lost gradually due to attrition. This is supported by the observation that a number of hematologic parameters in the peripheral blood are only modestly affected by ACK2 treatment (Table 1).

TABLE S1

Hematological effects of ACK2 treatment.

|  | Control | ACK2 |
| --- | --- | --- |
| Red Blood Cells (× $10^6$ cells/µL) | 9.92 | 8.21 |
| Hemoglobin (grams/dL) | 14.5 | 11.8 |
| Hematocrit (%) | 45.9 | 36.9 |
| Mean Corpuscular Volume (fL) | 46.3 | 45.0 |
| Mean Corpuscular Hemoglobin (pg) | 14.6 | 14.4 |
| Mean Corpuscular Hematocrit (g/dL) | 31.6 | 32.0 |

Moreover, significant numbers of both mature erythrocytes and regenerating erythroid colonies were observed in the bone marrow 9 days after ACK2 treatment (FIG. 6, bottom left panel). Additionally, both male and female mice treated with ACK2 remained fertile and had viable offspring. Thus, the side effects of antibody-mediated depletion of HSCs stand in marked contrast to lethal irradiation, which requires the early transplantation of bone 10 marrow or hematopoietic progenitors to prevent the death of the animal, a procedure which in humans is accompanied by high levels of morbidity and significant mortality.

Figure 8:
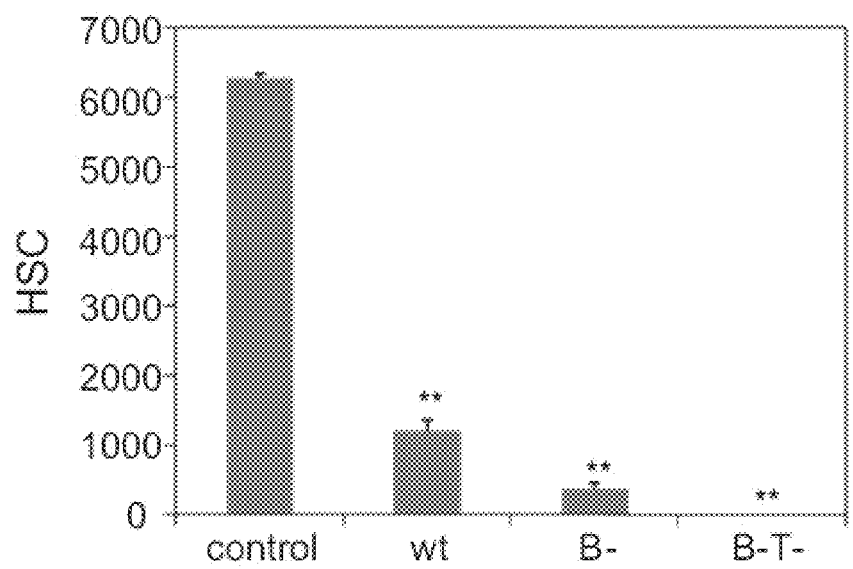
FIG. 8. ACK2 administration results in depletion of HSC in both wild type and immunodeficient mice. The number of KLS CD135$^-$CD150$^+$ HSCs in both femurs and tibia of ACK2-treated and control mice was determined by 22 flow cytometry 2 days after treatment with 1 mg of ACK2. Mean values +/−SEM are shown (n=2); ** indicates p-value<0.001.

Near complete HSC depletion was observed as early as two days post ACK2 administration. However, some HSCs clearly do remain and retain the capacity to self renew because by two weeks post-serum clearance of antibody, HSC cell surface profiles (FIG. 7) and numbers (FIG. 2B) had returned to near normal levels. Although ACK2 treatment does not directly cause host HSC mobilization (FIG. 2D), significant splenic extramedullary hematopoiesis does occur during the recovery phase by one week after ACK2 clearance (FIG. 7). By two weeks after clearance of ACK2 from the serum, the spleens of the animals appeared identical to untreated control animals. Wild-type mice as well as B cell-deficient µMT mice also showed decreased levels of HSCs in their bone marrow post ACK2 treatment (FIG. 8). Interestingly, the recovery of HSC numbers appeared to be more rapid in B cell-sufficient or T cell-sufficient animals after ACK2 clearance, suggesting an unexpected potential role for lymphocytes in stimulating hematopoietic recovery.

Figure 3A:
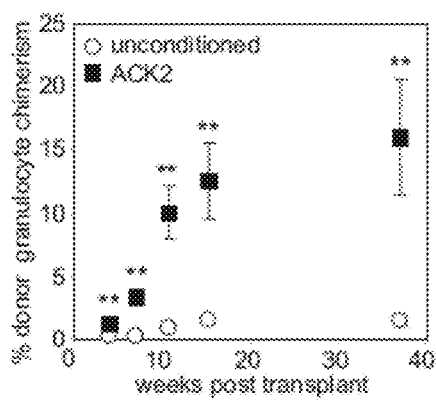
FIG. 3A-3D. ACK2 treatment enhances HSC engraftment.
Figure 3B:
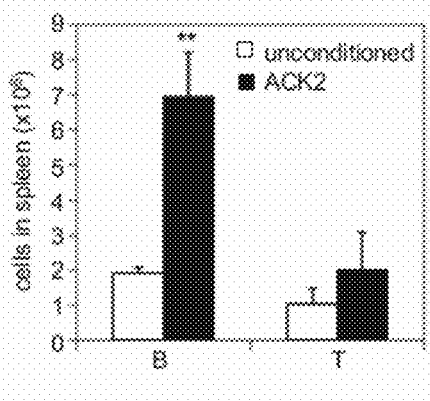
Figure 3C:
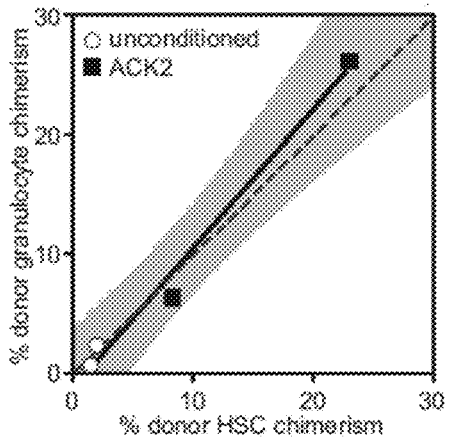

To test whether the ablation of host HSCs could improve the efficiency of donor HSC engraftment, we conditioned RAG2$^{-/-}$ (CD45.1) mice, which behave identically to RAG2$^{-/-}$µc$^{-/-}$ with respect to antibody treatment, with 500 µg ACK2. These mice were then transplanted with 5000 wild type CD45.2 LT-HSCs seven days post antibody administration, a time point at which there was no detectable ACK2 in the serum. Peripheral blood was obtained from the recipients every four weeks post transplantation and granulocyte chimerism was quantified. The mean donor granulocyte chimerism at 37 weeks post transplant was 16.1%, reflecting a >10-fold increase over untreated control animals that were transplanted with the same number of HSCs (FIG. 3A). The engrafted HSC also gave rise to donor-derived peripheral B cells and T cells (FIG. 3B). We also analyzed donor bone marrow HSC chimerism directly at this late time point to confirm the increase in donor engraftment, and indeed found that it correlated well with the donor peripheral blood granulocyte chimerism (FIG. 3C).

Figure 3D:
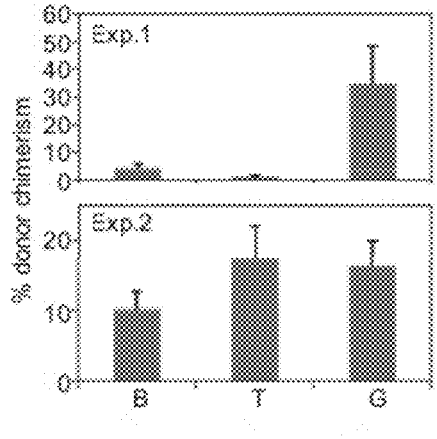
Figure 9:
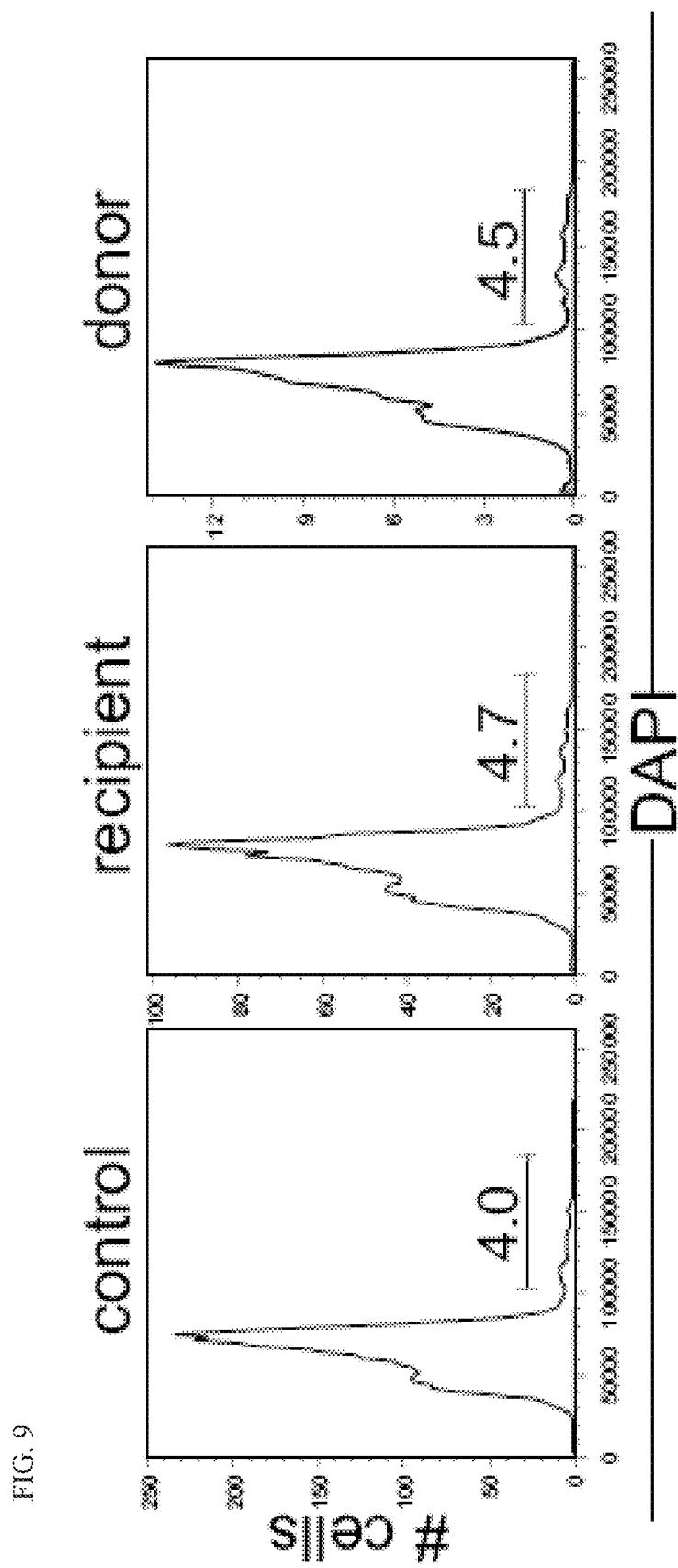
FIG. 9. Normal cell cycle status in recipient and donor HSCs after ACK2 treatment. Cell cycle profiles of untreated controls and both recipient and donor HSCs from ACK2-treated RAG2$^{-/-}$γc$^{-/-}$ mice that had been transplanted 7 months earlier with wild type HSCs were obtained. HSCs were identified as KLS CD150+CD34− cells.

Finally, to verify that we were accurately identifying functional donor HSCs with normal cell surface phenotypes, we re-isolated KLS CD34$^-$CD150$^+$ donor HSCs from the bone marrow of primary recipients and performed secondary transplants into irradiated recipient mice along with 200,000 wild type competitor bone marrow cells. These HSCs gave rise to multi-lineage engraftment for at least 16 weeks post-transplant (FIG. 3D), confirming that transplanted HSCs regain their normal cell surface phenotype by at least 7-9 months post-transplant in ACK2-treated animals. Consistent with this observation, we found that the cell cycle profiles of both host and donor HSCs in the BM of mice treated with ACK2 and transplanted 7 months prior was identical to that of untreated animals (FIG. 9).

Figure 4A:
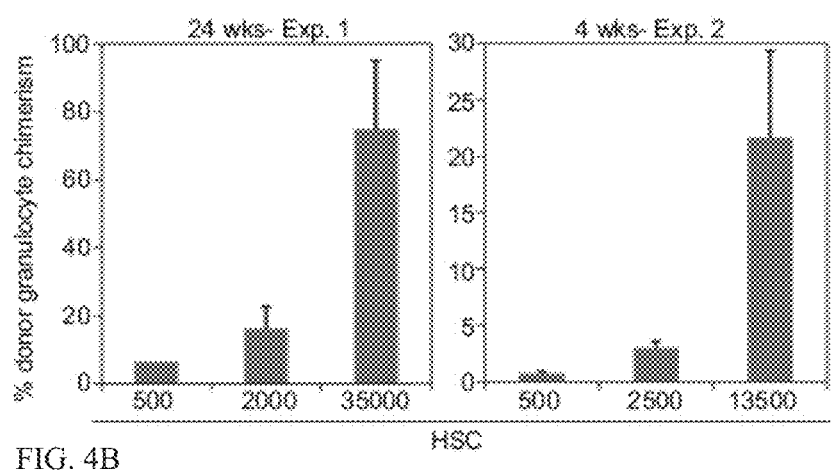
FIG. 4A-4B. Donor chimerism increases with transplanted HSC cell number in ACK2-treated mice.

These data indicate that through specific ablation of host HSCs, we were able to significantly increase donor HSC engraftment. However, it was unclear whether ACK2 treatment increased niche space, leading to a high level of initial HSC engraftment following transplantation, or whether, through the depletion of host HSCs, small numbers of initially engrafted donor HSCs in ACK2-treated mice could competitively expand. If niche space had truly been freed, HSC chimerism would be expected to increase with transplanted cell dose. In contrast, if the initial HSC engraftment were the same between ACK2-treated and unconditioned mice, no linear increase in donor chimerism would be expected at transplanted HSC numbers above 250 cells, as doses higher than this do not lead to linearly proportional increases in chimerism in unconditioned animals (FIG. 1). In order to determine the effects of cell dose in this system, we conditioned RAG2$^{-/-}$γc$^{-/-}$ (CD45.2) recipient mice with 500 µg ACK2 as above and transplanted them with varying doses of double-sorted CD45.1 LT-HSCs. Peripheral blood was assayed every four weeks for donor granulocyte chimerism until 24 weeks after transplantation. Donor engraftment increased linearly with transplanted HSC dose (FIG. 4A), and thus proved that the dose of transplanted HSCs required to saturate available niches had been significantly increased relative to unconditioned mice (FIG. 1). These data demonstrate that ACK2 treatment increases the proportion of niches available for engraftment, and that niche availability is regulated by host HSC occupation and that overcoming this barrier can allow high levels of donor HSC engraftment.

Figure 4B:
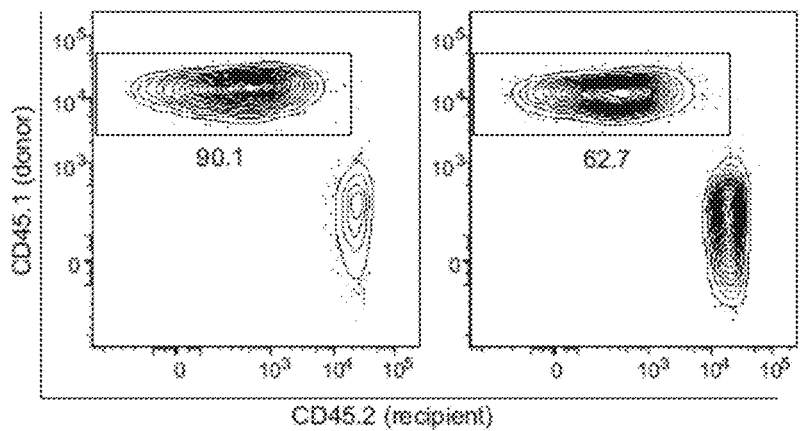

Previous studies that attempted to increase the number of available niches for transplantation by mobilizing endogenous HSCs may have failed due to the residual presence of mobilizing drugs at the time of transplantation or due to the damaging effects of these agents on the HSC-niche cells themselves. In the first experiment shown herein, both mice that received 35,000 HSCs (1.4×$10^6$ HSC/kg) had extremely high levels of donor chimerism (90.1% and 62.7% FIG. 4B). It is important to note that obtaining high numbers of HSCs has already proven to be clinically feasible, because most human HSC grafts are isolated from the peripheral blood of mobilized donors using regimens that lead to an expansion of HSCs. However, transplantation of such a large bolus of cells may be avoidable since similarly high levels of donor chimerism were consistently obtained through three rounds of conditioning and transplantation of 5000 HSCs (for a total of 15,000 transplanted HSCs) (FIG. 10). The total contribution of the third transplant was consistently higher than the first two HSC transplants combined.

Allogeneic BMT is used routinely for a number of clinical purposes, most commonly for the treatment of malignancies following high dose irradiation and chemotherapy, but also for the treatment of inherited hematopoietic deficiencies such as SCID. The minimum therapeutic levels of donor HSC chimerism vary between diseases, ranging from <1% for certain forms of SCID to ~20% for sickle cell anemia. Nevertheless, the minimum therapeutic level of chimerism may not be clinically optimal. For example, HSC chimerism levels of <1% in γc-deficient SCID patients can restore functional T cells, but B cells remain largely of host origin. Moreover, new T cell production correlates with myeloid chimerism and presumably HSC chimerism as well, suggesting that low levels of initial HSC engraftment lead to only finite periods of T cell production in SCID patients.

Here, we provide evidence that donor HSC engraftment is limited by the occupancy of appropriate niches by host HSCs. These data offer a clear explanation for the poor donor HSC engraftment observed in unconditioned SCID patients (Tjonnfjord et al. (1994) *Blood* 84, 3584; Muller et al. (2000) *Blood* 96, 4344).

The challenge for BMT, particularly for the treatment of non-malignancies, is maximizing the efficiency of donor HSC engraftment while minimizing harmful side effects. One of the major side effects associated with allogeneic BMT is graft versus host disease (GVHD), a potentially life-threatening condition in which the presence of alloreactive T cells within the graft leads to the destruction of host tissues. Importantly, studies have shown that purified allogeneic HSC transplantation does not cause GVHD. Other serious side effects of BMT are often associated with cytotoxic conditioning regimens. Even if employed in moderation through non-myeloablative conditioning, cytotoxic conditioning regimens carry significant health risks including infertility, prolonged thrombocytopenia, organ damage, immunosuppression and high rates of secondary malignancies. Indeed, it is these very side effects that prevent the routine clinical use of BMT for the treatment of serious but not immediately life threatening diseases such as sickle cell anemia and certain types of autoimmunity, which have been shown to be cured by HSC transplantation both in animal models and limited numbers of clinical cases.

We postulated that the most specific and consequently the safest way to increase HSC niche space would be through targeted antibody-mediated depletion. To generate preclinical evidence to support the use of HSC-depleting antibodies, we demonstrate above that administration of ACK2 in vivo leads to the rapid but transient depletion of host HSCs and progenitors. Transplantation of highly purified HSCs into ACK2-conditioned recipients leads to donor chimerism levels of up to 90%. These levels would almost certainly be therapeutic for inherited hematopoietic deficiencies. For SCID patients, the specific depletion of HSCs can be the only requirement of an effective conditioning regimen to allow for permanent and fully functional immune reconstitution by donor HSCs. For other types of inherited hematopoietic disorders, HSC-depleting antibody treatments in combination with specific immunosuppressive agents could potentially be employed in place of, or in combination with, lowered doses of drugs designed for myelosuppression. Thus, the use of HSC-depleting reagents is an attractive alternative to conventional methods of conditioning for BMT, and one which reduces the risks currently associated with bone marrow transplantation considerably, thereby increasing its utility in the treatment of a variety of hematologic and non-hematologic disorders.

Materials and Methods

Mice All animal procedures were approved by the International Animal Care and Use Committee. Recipient mice used in these studies were 4-8 weeks old recombinase activating gene 2-deficient ($RAG2^{-/-}$), $RAG2^{-/-}$interleukin-2 common gamma chain deficient ($RAG2^{-/-}\gamma c^{-/-}$) or μMT mice. Donor mice used were 8-12 weeks old GFP transgenic mice expressing GFP from the chicken β-actin promoter, or congenically distinguishable CD45.1 or CD45.2 C57Bl/Ka mice. All mouse strains were bred and maintained at Stanford University's Research Animal Facility.

HSC Transplantation Bone marrow was harvested from donor mice by crushing bones, lysing red blood cells with ACK lysis buffer (150 mM NH4Cl, 1 mM KHCO3, and 0.1 mM EDTA), and removing debris on density gradient using Histopaque 1119 (Sigma, St. Louis, Mo.). Bone marrow was then c-kit+ enriched using CD117+ microbeads (AutoMACS, Miltenyi Biotec, Auburn, Calif.). Cells were stained with antibodies described below and HSC were isolated by single or double FACS based on previously defined reactivity for particular cell surface markers ($c-kit^+$ ineage$^-$Sca-1+CD34$^-$CD150+) on the BD FACS-Aria (BD Biosciences, San Jose, Calif.). Cells were transplanted by retro-orbital injection.

Antibodies The following monoclonal antibodies were purified and conjugated using hybridomas maintained in our laboratory: 2C11 (anti-CD3), GK1.5 (anti-CD4), 53-6.7 (anti-CD8), 6B2 (anti-B220), 8C5 (anti-Gr-1), M1/70 (anti-Mac-1), TER119 (anti-Ter119), A20.1.7 (anti-CD45.1), AL1-4A2 (anti-CD45.2), 2B8 (anti-c-kit), 3C11 (anti-c-kit), E13-161-7 (anti-Sca-1). Antibodies were conjugated to biotin, Pacific Blue, Pacific Orange, PE, allophycocyanin (APC), Alexa 488, Alexa 647 or Alexa 680 (Invitrogen, Carlsbad, Calif.), according to the manufacturer's instructions. The following were purchased from eBiosciences (San Diego, Calif.): antibodies against CD3, CD4, CD8, B220, Mac-1, Ter119, and Gr-1 conjugated to PE-Cy5; anti-c-kit and anti-Mac-1 conjugated to PECy7; anti-CD135 (A2F10) conjugated to PE; anti-CD34 conjugated to FITC or biotin; and anti-B220 conjugated to APC-Cy7. Anti-CD41 conjugated to FITC, anti-CD48 conjugated to FITC, goat-anti-rat conjugated to APC, and anti-TCRB (H57-597) conjugated to APC were purchased from BD Biosciences. Anti-CD150 conjugated to Alexa 647 was purchased from Biolegend (San Diego, Calif.). Streptavidin conjugated to Alexa 488 and Alexa 680, and goat-anti-rat conjugated to Alexa 488 was purchased from Invitrogen. Streptavidin conjugated to Quantum Dot 605 was purchased from Invitrogen.

ACK2 Production and Purification The ACK2 hybridoma was a gift. The cell line was expanded and subcloned to establish an ACK2 high producing hybridoma cell line. Cells were grown in the Integra flask system (Integra Biosciences, Chur, Switzerland) and media containing antibody was collected. ACK2 was purified on an IgG purification column by binding the ACK2 to the column and eluting with 100 mM Glycine and 5 mM $NaN_3$. The eluted positive fractions (OD280 >0.2) were combined, dialyzed for 12 hours in PBS, and concentrated using a Vivaspin concentrator (Sartorius AG, Goettingen, Germany). Subsequent ACK2 preparations were prepared by Bio Express (W. Lebanon, N.H.).

ACK2 Administration and Clearance 500 μg of ACK2 was administered through retro-orbital injection to 4-8 week RAG2$^{-/-}$γc$^{-/-}$ mice. Peripheral blood was isolated from the tail vein of these mice every other day and allowed to clot for 1 hour. Samples were centrifuged for several minutes and serum was isolated. 10,000 mast cells were subsequently stained with 50 μl of serum, followed by goat-anti-rat IgG APC or Alexa 488, to test for ACK2 antibody presence. In addition, mast cells were stained with a known anti-c-kit antibody, 2B8 conjugated to APC as a control. These cells were analyzed on the BD FACS-Aria. To determine HSC depletion, both femurs and tibia were obtained from conditioned mice and prepared as above. Cells were counted and HSC frequency was determined on the BD FACS-Aria by gating on KLS CD135$^-$CD150$^+$ cells.

ACK2 Conditioning and Transplantation 500 μg of ACK2 was administered intravenously to 4-8 week Rag2$^{-/-}$or Rag2$^{-/-}$γc$^{-/-}$ mice. Mice were transplanted at the time point that ACK2 was shown to no longer be present in the serum (D7 or D9 depending on preparation). HSC for transplantation were obtained from bone marrow of donor mice, which were isolated on the BD FACSAria by gating on c-kit$^+$lineage$^-$Sca-1$^+$CD34$^-$CD150$^+$ cells.

Engraftment Analysis Blood was obtained from the tail vein of transplanted mice at various time points. It was separated using 2% dextran at 37° C. for 30 min, and subsequently lysed using ACK lysis buffer (150 mM NH4Cl, 1 mM KHCO3, and 0.1 mM EDTA) for 5 minutes. Cells were stained with antibodies described above and analyzed on the BD FACS-Aria. Donor granulocyte chimerism was determined by analyzing the percentage of Ter119$^-$CD3$^-$B220$^-$Mac1$^{high}$ side scatter$^{high}$ cells that were also donor$^+$. Several animals were sacrificed and HSCs were isolated similarly to donor mice in order to confirm that the HSC chimerism mimicked the granulocyte chimerism. To determine the effects of ACK2 on hematopoietic progenitors, bone marrow was isolated from mice treated with 500 μg ACK2 as above. Cells were counted and progenitor frequency was determined on the BD FACS-Aria. Cell numbers were compared to those of untreated animals. HSC were gated as lin$^-$c-kit$^+$Sca-1$^+$CD135$^-$CD150$^+$, MEP were gated as lin$^-$c-kit$^+$Sca-1$^-$CD34$^-$FcγR$^-$, CMP were gated as lin$^-$c-kit$^+$Sca-1$^-$CD34$^{low}$FcγR$^{low}$, and GMP were gated as lin$^-$c-kit$^+$Sca-1+CD34$^{high}$FcγR$^{high}$.

Transplantation into Irradiated Recipients Recipient mice were treated with 950 cGy prior to transplantation. Each mouse was transplanted with the entire splenocyte population from an ACK2 mouse treated 9 days prior, 200,000 unfractionated bone marrow cells from an ACK2 mouse treated 9 days prior, or 100 donor$^+$ KLS CD34$^-$CD150$^+$ HSC from a primary transplanted mouse (ACK2 conditioned and transplanted with 5000 donor HSC 39 weeks prior).

In Vitro Culture Exactly 10 HSCs (KLS CD34-CD150+) were clone sorted on the BD-Aria into 96-well round-bottom plates and cultured in the presence of 50 ng/ml SCF (R&D Systems) or 50 ng/ml TPO (R&D Systems) in Iscove's Modified Dulbecco's Medium (Invitrogen) with 10% fetal calf serum (Omega), 1 mM sodium pyruvate (Invitrogen), 100 μM nonessential amino acids (Invitrogen), and 50 μM β-mercaptoethanol. HSC treated with antibody received 10 μg/ml of ACK2 or 2B8. Viable cells were counted each day under the microscope.

Cell Cycle Analysis Bone marrow cells were c-kit-enriched as before and stained with anti-CD34 FITC, antic-kit (2B8) PE-Cy7, anti-CD150 Alexa 647, anti-Sca-1 Alexa 680, and anti-lineage PECy5. Cells were then fixed with 2% paraformaldehyde in PBS for 20 minutes at room temperature, washed twice with PBS, and resuspended in PBS/0.2% saponin+2 μg/ml 4',6-diamidino-2-phenylindole (DAPI) prior to analysis.

Histology Mice were treated with 500 μg ACK2 and at 2 days and 9 days post treatment, the humerus was removed and placed in Bouin's fixative for >1 day. Bones were decalcified in formic acid, paraffin-embedded, sectioned, stained with hematoxylin and eosin, and mounted using xylene-based media.

Analysis of peripheral blood Peripheral blood was collected from the tail vein and deposited directly into heparincoated tubes. Analysis was performed by the Department of Comparative Medicine's Diagnostic Laboratory at Stanford University.

Example 2

Figure 11:
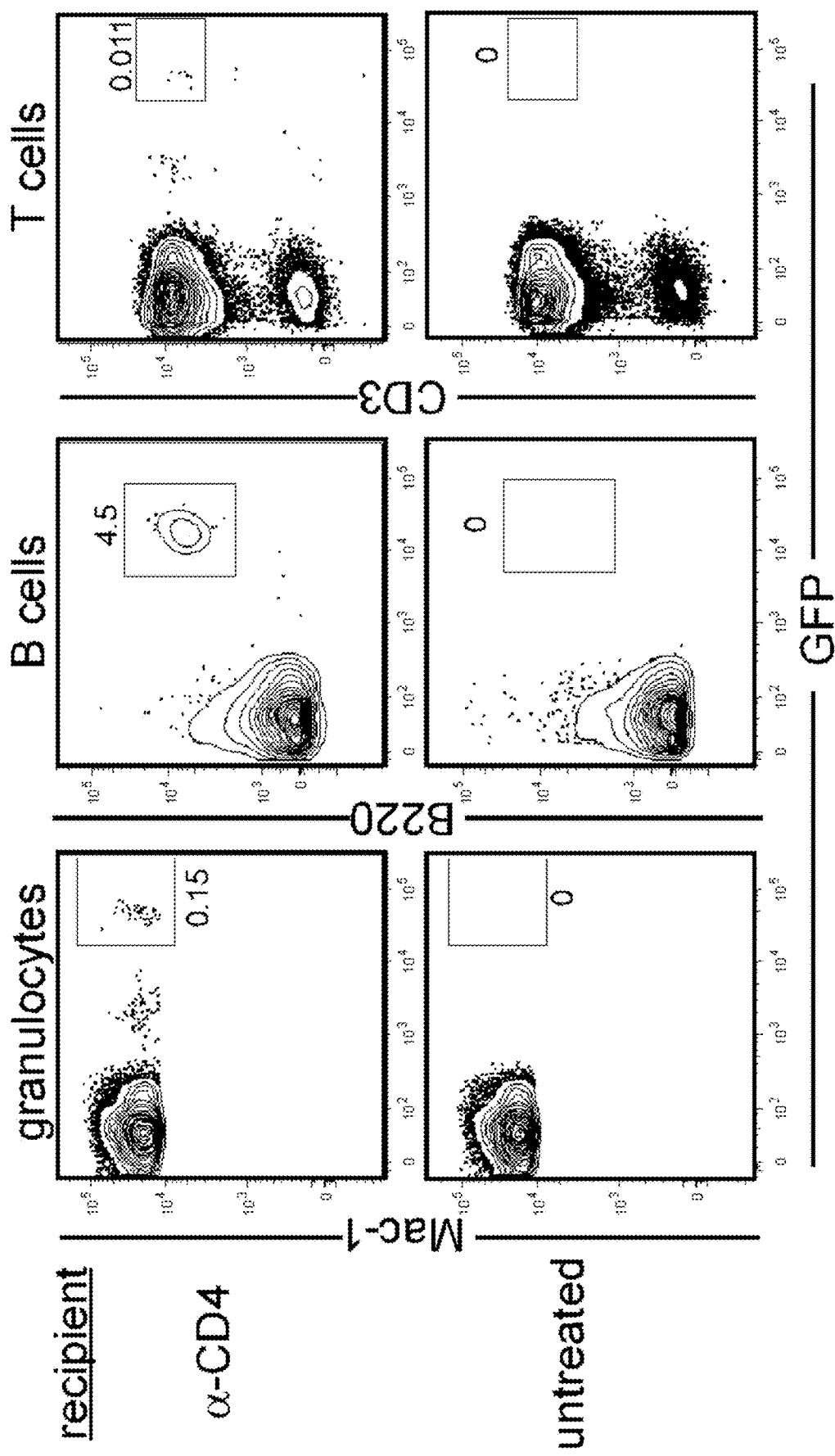
FIG. 11. Transient CD4 depletion allows productive engraftment of HSC with minor histocompatibility mismatches. Three Cμ$^{-/-}$ mice that were treated with anti-CD4 antibody and two Cμ$^{-/-}$ mice that were left untreated were transplanted with 800 GFP+ HSC. Peripheral blood was analyzed at 8 weeks after transplantation for granulocyte, B cell, and T cell chimerism.

Antibody-Mediated Lymphoablation and HSC Transplantation for the Treatment of Agammaglobulinemia We sought to determine whether transient depletion of CD4+ T cells from mice that normally reject allogeneic HSCs would allow for minor histocompatibility-mismatched HSC engraftment. Cμ$^{-/-}$ mice, which are a model for agammaglobulinemia and are recalcitrant to sustained donor HSC engraftment in the absence of irradiation, were treated with anti-CD4 antibody (clone GK1.5), which depletes >95% of CD4+ T cells in vivo, prior to transplantation with HSCs from GFP-transgenic mice. Short-term engraftment and B cell reconstitution was seen in all animals treated with anti-CD4 antibody, but was never seen in any of the untreated animals (FIG. 11). This chimerism, however, was lost between 8-12 weeks after transplantation as CD4+ T cell counts returned to normal. Thus, in this system, permanent transplantation tolerance was not generated by ~0.1-0.2% HSC chimerism.

Candidate human HSC-specific depleting antibodies. Candidate antibodies specific for markers expressed by human HSCs, including c-kit (clone BA7.3C.9, IgG2a), CD133 (clone AC133.1, IgG1), and c-mpl (clone BAH-1, IgG1), are purchased as hybridomas from the American Type Culture Collection or as purified solutions from other vendors. Approximately 100-500 μg of these antibodies are injected into NOD-SCID/γc$^{-/-}$ mice that have been transplanted 4-6 weeks prior with ~10,000 human cord blood HSCs. Peripheral blood myeloid chimerism is measured at 2, 4, and 6 days after antibody treatment. At 7 days posttreatment, mice are sacrificed and the number of phenotypic human HSCs in the marrow of treated and untreated mice is quantified. Antibodies that have a specific depleting effect effect a dramatic reduction in myeloid chimerism and in the number of engrafted human HSCs. Recombinant versions of the variable region may be combined with a mouse Cy2b constant region, since IgG2b class antibodies are the most effective isotype at binding complement, and also are active in ADCC and opsonization. The isotype of the mouse ACK2 Mab is IgG2b. These recombinant antibodies are tested in vitro by staining and then incubating human cord blood or bone marrow with purified mouse complement. The specific depletion of human HSCs is verified by flow cytometry.

Candidate antibodies capable of depleting human HSCs are tested for depletion that creates additional niche space for newly transplanted human HSCs. Approximately 7 days after antibody treatment of xenochimeric mice, these mice and control xenochimeric mice that have not been treated with the depleting antibody are retransplanted with ~10,000 HLA-distinguishable cord blood HSCs. If additional niche space has been created by the removal of HSCs from the first transplant, the chimerism arising from the second transplant should be considerably higher in the antibody-treated mice.

Example 3

Purified Hematopoietic Stem Cell Engraftment of Rare Niches Corrects Severe Lymphoid Deficiencies without Host Conditioning In the absence of irradiation or other cytoreductive conditioning, endogenous hematopoietic stem cells (HSCs) are thought to fill the unique niches within the bone marrow that allow maintenance of full hematopoietic potential and thus prevent productive engraftment of transplanted donor HSCs. By transplantation of purified exogenous HSCs into unconditioned congenic histocompatible strains of mice, we show that ~0.1-1.0% of these HSC niches are available for engraftment at any given point and find no evidence that endogenous HSCs can be displaced from the niches they occupy. We demonstrate that productive engraftment of HSCs within these empty niches is inhibited by host CD4+ T cells that recognize very subtle minor histocompatibility differences. Strikingly, transplantation of purified HSCs into a panel of severe combined immunodeficient (SCID) mice leads to a rapid and complete rescue of lymphoid deficiencies through engraftment of these very rare niches and expansion of donor lymphoid progenitors. We further demonstrate that transient antibody-mediated depletion of CD4+ T cells allows short-term HSC engraftment and regeneration of B cells in a mouse model of B(−) non-SCID. These experiments provide a general mechanism by which transplanted HSCs can correct hematopoietic deficiencies without any host conditioning or with only highly specific and transient lymphoablation.

Immune surveillance prevents engraftment of subtly mismatched HSCs. HSCs in 4,000 ckit+ Thy1.1low lineage– Sca-1+ Flk2– CD34– cells from CD45.1 mice were transplanted intravenously into five unnirradiated CD45.1× CD45.2 (F1) and five unirradiated congenic CD45.2 mice. Every 4 wk after transplantation, peripheral blood was analyzed for granulocyte, B cell, and T cell chimerism. Donor granulocyte chimerism, which accurately reflects HSC chimerism, was observed only in the genetically unreactive F1 recipients at all time points analyzed with a median chimerism at 16 wk of ~0.1%. These data demonstrate that the subtle antigenic differences that exist between these CD45 congenic strains of mice are sufficient to prevent productive HSC cross-engraftment.

Rapid HSC-mediated correction of lymphoid deficiencies in SCID mice. To gauge the potential clinical importance of these rare available niches, we repetitively transplanted HSCs from GFP-transgenic mice into RAG2 and IL-2 receptor common γ chain-deficient (RAG2−/−γc−/−) mice, which lack B, T, and NK cells. Enormous numbers of donor-derived B and T cells were found in the blood at all time points, leading to an overall donor chimerism of ~50% until at least 30 wk after the final transplantation. Donor NK cells were also detected in all transplanted animals. Moreover, all RAG2−/−γc−/− mice displayed persistent donor-derived myeloid chimerism (ranging from 0.5 to 2.0% donor-derived granulocytes).

To confirm that the donor granulocyte frequencies accurately reflected bone marrow HSC chimerism, we killed animals at 30 wk after transplant and analyzed bone marrow. Donor cells comprised ~0.8% of the total long-term (LT)-HSC pool. This chimerism was essentially the same in the short-term reconstituting stem cells (ckit+ lineage– Sca-1+ CD34+ Flk2–) and the multipotent progenitors (ckit+ lineage– Sca-1+ CD34+ Flk2+). We were unable to detect any cells with these surface phenotypes in the spleen, a major organ associated with extramedullary hematopoiesis. These data confirmed that in these animals, peripheral donor granulocyte frequencies much more accurately reflect HSC chimerism than the overall donor contribution in the blood. The data also demonstrate that small numbers of bone marrow-engrafted HSCs can correct severe lymphoid deficiencies without prior cytoreductive conditioning. The HSC chimerism in the RAG2−/− {gamma}c−/− mice was comparable to the chimerism seen in the genetically unreactive F1 wild-type mice, demonstrating that there are not obviously greater numbers of available HSC niches in these animals.

To confirm that functional HSCs had engrafted, we isolated bone marrow at 31 wk after transplant from unirradiated RAG2−/−γc−/− mice that had received GFP+ HSC transplants and performed secondary transplants using either unfractionated or c-kit-enriched marrow, which increases the frequency of HSCs by ~10-fold, into lethally irradiated wild-type mice, such that ~6-20 GFP+ HSCs along with 1,000 RAG2−/−γc−/− HSCs were transferred into each secondary recipient. Donor-derived GFP+ cells were observed in all secondary recipients until at least 25 wk after transplantation, and 6 out of 13 secondary recipients maintained detectable levels of granulocyte chimerism. These data confirmed that rare GFP+ HSCs within the bone marrow of the primary RAG2−/−γc−/− recipients had productively engrafted. In contrast, transplantation of large numbers of splenocytes into secondary recipients did not lead to sustained multilineage stem cell reconstitution.

Opportunistic expansion of donor lymphoid progenitors. To determine the developmental stage at which donor B cells overtake host B cells in RAG2−/−γc−/− recipients, we analyzed donor frequencies in myeloid and lymphoid progenitor cells in the bone marrow. Common myeloid progenitors (CMPs) and common lymphoid progenitors (CLPs) showed donor chimerism that was comparable to HSC chimerism, indicating that donor-derived cells do not have a competitive proliferative advantage at these early developmental steps. Donor chimerism at the granulocyte macrophage progenitor (GMP) and megakaryocyte erythrocyte progenitor (MEP) developmental steps were also similar to HSC chimerism. Consistent with these results, the frequencies of endogenous HSCs, CLPs, CMPs, GMPs, and MEPs within the bone marrow are similar between untransplanted wild-type and RAG2−/− γc−/− mice. Analysis of the pro-B-A and pro-B-B cell fractions, however, showed donor chimerism that was dramatically higher than the preceding CLP. At the pro-B-B cell stage and all subsequent B cell stages, cells were exclusively donor-derived. Although IL-7 receptor, which uses γc for proper signaling, is expressed at the CLP stage, these results suggest that IL-7 signaling is not a requisite pathway for CLP development or expansion, consistent with previous observations.

Normal immune responses in HSC-reconstituted SCID mice. To verify that the immune system of the HSC-reconstituted RAG2−/−γc−/− mice had been restored and was capable of mounting appropriate immune responses, we immunized reconstituted recipients with alum-precipitated 4-hydroxy-3-nitrophenylacetyl (NP) conjugated to chicken {gamma} globulin, which elicits a Th2-dependent humoral response. Serum levels of NP-specific antibody were similar at 1 wk after immunization between HSC-transplanted RAG2−/−γc−/− and wild-type mice, demonstrating the immunocompetence of the transplanted RAG2−/−γc−/− recipients.

Host CD4+ T cells are essential for rejection of subtly mismatched HSCs. To investigate whether the absence of γc was critical for HSC engraftment in unconditioned hosts, perhaps by imparting a competitive disadvantage on HSCs in RAG2−/−γc−/− animals, we transplanted GFP+ HSCs into RAG2−/− mice, which have normal {gamma}c expression, as well as into RAG2−/−γc−/− mice. Similar levels of donor granulocyte contribution were seen in RAG2−/− and RAG2−/−γc−/− mice, likely excluding a direct role for γc in maintaining host HSCs within their niches. However, γc expression has been observed in normal HSCs, suggesting that there may be a slight competitive advantage for HSCs with proper γc expression. The data also suggest that NK cells, which are present in normal numbers in RAG2−/− mice but absent in RAG2−/−γc−/− mice, are not mediating HSC rejection in this H2-identical system. Elimination of host NK cells is required for engraftment of HSCs that carry one or more unshared H2 haplotype. Interestingly, donor-derived lymphocyte frequencies were significantly reduced in RAG2−/− recipients at early time points (FIG. 7 B), perhaps as a result of the occupation of the lymphoid stage-specific stromal environments by RAG2−/− lymphoid progenitors. The number of donor-derived B cells in RAG2−/− recipients was reduced more than 10-fold relative to RAG2−/−γc−/− recipients at 4 wk after transplant, and peripheral T cells were not seen at all until 8 wk after transplant. However, by 16 wk after transplantation, B and T cell numbers in RAG2−/− recipients reached the levels seen in their RAG2−/−γc−/−counterparts.

Because RAG2−/− mice lack both mature B and T cells, we sought to determine which of these cell types was primarily responsible for mediating the rejection of transplanted donor HSC grafts. Therefore, we transplanted purified HSCs from GFP donor mice into unnirradiated TCRα−/−β−/− and Cμ−/− mice. In these experiments, known antigenic differences between donor HSCs and recipient mice exist at the GFP, CD45, and Thy1 loci. Multilineage engraftment was observed in T cell-deficient mice, but not in B cell-deficient mice. These experiments show that host αβ T cells are required for the rejection of HSC grafts with these minor histocompatibility mismatches. To determine which class of T cells is essential for this immunosurveillance, we transplanted HSCs into unconditioned I-A−/− mice, which lack MHC II-restricted CD4+ T cells, and 132-microglobulin−/− (β2m−/−) mice, which are deficient in MHC I-restricted CD8+ T cells. The HSC-transplanted I-A−/− mice showed sustained chimerism until at least 16 wk, whereas the 132m−/− recipient mice did not show chimerism at any time point, thereby demonstrating that CD4+ T cells are essential for the rejection of minor histocompatibility-mismatched HSC grafts in our system. LT-HSCs express MHC II and the costimulatory molecule CD86, suggesting that host CD4+ T cells may directly recognize HSCs with slight antigenic mismatches. Although it appears that CD8+ T cells are not required for this rejection, we cannot exclude the possibility that residual hyperreactive MHC I-restricted T cells might also contribute to HSC graft rejection in the β2m−/− mice. Consistent with the role for CD8 T cells in mediating bone marrow graft rejection, Xu et al. have shown that host CD8 deficiency enhances engraftment.

Interestingly, the granulocyte chimerism in the RAG2−/− recipients was indistinguishable from that seen in previous experiments in which 3,000 HSCs rather than 1,000 were transplanted. In contrast, although transplantation of 20 HSCs led to detectable B and T cell production in these immunodeficient mice, granulocyte chimerism was barely detectable. Thus, our experiments suggest that HSC engraftment and chimerism asymptotically approaches a maximum of ~0.5% in a cell dose-dependent manner. The data show that in contrast to previous speculations, endogenous HSCs cannot be displaced from the niches they occupy by increasing transplanted HSC numbers above a threshold level. In repetitively transplanted mice, however, we have observed small increases in granulocyte chimerism relative to mice that were HSC-transplanted only once with doses above this threshold. This provides evidence that transplantation of an excess of HSCs does not preclude additional niches from being vacated in the future.

To determine if transient CD4+ T cell removal would allow access of transplanted HSCs to appropriate niches, we treated Cμ−/− mice with a depleting CD4 antibody that led to ~95% depletion of peripheral blood CD4+ T cells. CD4-depleted mice were then transplanted with 800 HSCs and analyzed at various time points for donor chimerism. All mice that received anti-CD4 treatment showed donor granulocyte chimerism, whereas none of the untreated mice displayed any detectable donor cells at 8 wk after transplantation. Significant numbers of donor B cells were observed in the treated mice at 6-8 wk after transplantation, again demonstrating the ability of small numbers of productively engrafted HSCs to restore lymphocyte numbers in immunodeficient mice. Because host CD4+ T cells levels were noted to recover subsequent to immunodepletion, these experiments demonstrate that transient depletion of these cells before transplantation is sufficient to allow for productive short-term stem cell engraftment without the need for the standard toxic cytoreductive drugs commonly used for B(−) non-SCID patients before bone marrow transplant. However, by 12 wk after HSC transplantation, donor B cell, T cell, and myeloid chimerism was lost in all recipient mice. These data suggest that either the α-CD4-mediated depletion of mature T cells was incomplete, or that sufficient numbers of donor-derived dendritic cells were not generated to mediate lasting tolerance through negative selection in the thymus.

Short-term reconstitution in unconditioned aged recipients. Aged individuals show marked reductions in thymus size and T cell function. To determine if the reduced lymphoid function in aged mice would allow acceptance of transplants without conditioning, we repetitively transplanted HSCs from GFP-transgenic mice into old (22 mo) and young (2 mo) recipients. Short-term low-level myeloid chimerism was observed in all old recipients in contrast to the young recipients that showed no engraftment. However, donor-derived cells declined to undetectable levels in all but one of the old recipients with time, suggesting that rejection of the transplants did occur, but with significantly reduced kinetics relative to the younger animals. The level of granulocyte chimerism in this experiment was similar to the low levels seen in transplants of younger, genetically unreactive or immunodeficient mice, suggesting that aged HSCs cannot be displaced from their endogenous niches. This is in contrast to previous studies performed with unfractionated bone marrow transplants and suggests that reduced immune capacity is responsible for short-term engraftment of donor HSCs.

The remarkable ability of HSCs to sustain multilineage hematopoiesis for the lifetime of an individual constitutes the foundation for their routine use in a range of clinical applications, including the treatment of primary immunodeficiencies, malignancies, as conditioners for transplantation tolerance of tissue or organ grafts from the donors, and as a method to reverse some types of autoimmunity. The success of such therapies relies on the ability of HSCs to home to unique niches leading to sustained multilineage hematopoiesis.

The studies presented here have quantified the number of these HSC niches that are available for engraftment at any given point in unconditioned animals as ~0.1-1.0% of all HSC niches. Assuming a total adult murine bone marrow cellularity of $5 \times 10^8$ cells and an endogenous HSC frequency of 0.01%, the number of open HSC niches can be estimated to be 50-500. This is strikingly similar to the number of HSCs estimated to be in circulation at any given point. The data suggest that HSCs that circulate normally have exited and left vacant their previous HSC niche. Thus, a constant exchange may be occurring between endogenous HSCs under normal circumstances, perhaps to maintain hematopoietic balance between and within each bone marrow compartment.

In support of this, we have found little difference in the granulocyte chimerism rates between experiments when a single transplant of HSCs is provided in doses ranging from 800 to 4,000 cells. Although previous reports have suggested that the cell doses of transplanted bone marrow correlate with total chimerism linearly, such data at most show replacement of bone marrow and mature cells in bulk and do not reflect replacement of HSCs, which represent only 0.01% of unfractionated marrow. When HSCs are repetitively transplanted, however, we have observed increases in granulocyte chimerism. Thus, occupation of available HSC niches after transplantation of an excess of exogenous HSCs, which remain in circulation for ~1-5 min after transplantation, does not preclude additional niches from becoming available subsequently. Conceivably, continuous transfusion of low numbers of HSCs would be superior to singly administered boluses, as the rate of niche emptying and filling is high. Because there does not appear to be an obvious increase in granulocyte chimerism with time or cell dose above a threshold level, the data also suggest that transplanted HSCs must find their way rapidly to an appropriate niche and cannot recirculate indefinitely in search of empty niches without the loss of hematopoietic potential.

The ability of transplanted HSCs to self-renew for the lifetime of the organism ensures a constant production of normal lymphoid cells through each developmental stage. In the genetic mutants used in our work, host lymphocyte development is blocked or perturbed at defined developmental stages. At each developmental stage or thereafter, wild-type donor cells have a competitive advantage and can opportunistically expand or accumulate to ultimately give rise to large numbers of normal mature lymphocytes. Several factors have been implicated in the expansion of the early B cell and thymocyte lineages, including IL-7, stem cell factor, Flt3 ligand, and recently, various Wnt/Frizzled pathways. In the case of γc−/− animals, the pro-B-B population appears to have defects in IL-7-dependent expansion, providing a proliferative advantage to wild-type donor cells at these stages. RAG2−/− mice likely reconstitute more slowly because their lymphocytes can develop normally through the pro-B cell as well as DN3 thymocyte stages and occupy the appropriate stromal microenvironments. However, because RAG2−/− lymphocytes cannot advance past these stages, small numbers of developing donor-derived cells can expand and accumulate without competition at the pre-B as well as DN4 thymocyte cell stages and all subsequent developmental steps. We have observed no meaningful decline in granulocyte or lymphocyte chimerism at any time point up to 30 wk after transplantation of primary recipients.

We also show conclusively that stable engraftment within these rare niches by minor histocompatibility-mismatched HSCs is tightly regulated by host CD4+ T cells. HSCs from CD45.1 mice cannot productively engraft unirradiated congenic CD45.2 mice, yet they routinely engraft the genetically unreactive F1 strain (CD45.1×CD45.2). To our knowledge, the only antigenic difference between these strains is the CD45 allele, which is normally considered to be a relatively innocuous congenic marker. Similarly, HSCs isolated from GFP-transgenic mice backcrossed to the C57BL/Ka genetic background cannot productively engraft wild-type C57BL/Ka mice. The only antigenic difference between these strains to our knowledge is the GFP gene product.

Encouragingly, however, the elimination of CD4+ T cell function allows for the functional and sustained engraftment of HSCs with minor histocompatibility mismatches in our system. We demonstrate that transient antibody-mediated CD4+ T cell depletion alone is sufficient to allow short-term engraftment of wild-type donor HSCs and restoration of B cells in a mouse model of non-SCID. More complete CD4+ T cell depletions and/or better methods to increase donor-derived thymic dendritic cell contribution might allow for lasting donor hematopoiesis.

Even in the absence of inherited genetic mutations, both mice and humans develop diminished immune capacity with age. This progressive loss of immune function has recently been attributed to HSC-intrinsic defects in differentiation to lymphoid-primed progenitors. Because we have demonstrated that a very small number of properly functioning HSCs can mask the defects in a much larger pool of HSCs, it is tempting to speculate that age-related immune defects don't become readily apparent until nearly all fully "young" HSCs are exhausted. The reintroduction of fully multipotent HSCs, perhaps obtained as an autologous sample earlier in life, might significantly delay age-related immune decline.

The mechanism by which transplanted HSCs correct hematopoietic deficiencies in our unconditioned recipients is applicable to the correction of many types of both SCID and non-SCID immunodeficiencies, but these studies at the same time clearly demonstrate that very subtle minor histocompatibility differences can mediate the rejection of HSC grafts when host T lymphocytes are present. Our data suggest that transplantation of purified HSCs, in combination with highly specific lymphoablative treatments when necessary, can correct lymphoid deficiencies in immunodeficient patients without the undesired side effects, such as toxic conditioning and GVHD, often associated with current conditioning and transplantation regimens.

Materials and Methods

Animals. All animal procedures were approved by the International Animal Care and Use Committee. C57BL/Ka-Thy1.1 CD45.2+(HZ) and C57BL/Ka-Thy1.1 CD45.1 (BA) strains were derived and maintained in our laboratory. eGFP transgenic mice used in these studies were backcrossed at least 20 generations to either the BA or HZ strain. C57Bl6/

Harland mice used for the aging studies were obtained from the National Institute of Aging. The RAG2−/−, RAG2−/−γc−/−, I-A−/−, and β2m−/− mice have been described previously and were bred at least 20 generations onto the C57BL/Ka-Thy1.2 CD45.1+, C57BL/Ka-Thy1.2 CD45.2+, and C57BL/Ka-Thy1.1 CD45.2 backgrounds. TCRα−/−β−/− mice were provided by J. Campbell and M. Davis (Stanford University, Stanford, Calif.). Cμ−/− mice were provided by J. Tung and L. Herzenberg (Stanford University). Peripheral blood was sampled from the tail vein, and all HSC transplants were performed by injection into the retroorbital sinus of isoflurane-anesthetized mice. For repetitive transplants, between 1,750 and 4,000 HSCs were transplanted weekly for 6 wk. Donor mice were 4-6-wk old, and recipient mice ranged from 4-12 wk of age unless otherwise noted.

Antibodies. The following monoclonal antibodies were purified and conjugated using hybridomas maintained in our laboratory: 19XE5 (anti-Thy1.1), 2C11 (anti-CD3), GK1.5 (anti-CD4), 53-7.3 (anti-CD5), 53-6.7 (anti-CD8), 6B2 (anti-B220), 8C5 (anti-Gr-1), M1/70 (anti-Mac-1), TER119 (anti-Ter119), A20.1.7 (anti-CD45.1), AD-4A2 (anti-CD45.2), 2B8 (anti-c-kit), E13-161-7 (anti-Sca-1), anti-CD16/CD32 (2.4G2), and A7R34 (anti-IL-7 receptor {alpha}). Antibodies were conjugated to biotin, PE, allophycocyanin (APC), Alexa 405, Alexa 430, or Alexa 488 (Invitrogen), according to the manufacturer's instructions. The following were purchased from eBiosciences: antibodies against CD3, CD4, CD8, B220, Mac-1, Ter119, and Gr-1 conjugated to PE-Cy5; anti-c-kit and anti-Mac-1 conjugated to PE-Cy7; anti-Sca-1 conjugated to PE-Cy5.5; anti-CD45.1 and anti-CD45.2 (104) conjugated to APC-Cy5.5; anti-B220 conjugated to APC-Cy7; anti-Flk2 (A2F10) conjugated to PE or biotin; and streptavidin conjugated to APC. Anti-CD34 (RAM34) conjugated to FITC or biotin, anti-TCRβ (H57-597) conjugated to APC, anti-CD43 (1B11) conjugated to PE, anti-I-A/I-E (M5.114.15.2) conjugated to PE, and anti-Ly51 (6C3) conjugated to biotin were purchased from BD Biosciences. Streptavidin conjugated to APC-Cy7 was purchased from Caltag.

FACS and analysis. All cells were sorted on a FACSVantage or a FACS Aria (Becton Dickinson). All peripheral blood analysis was performed on an LSR-Scan (Becton Dickinson). Peripheral blood was obtained from the tail vein, red blood cells were sedimented with 2% dextran, and the remaining red blood cells were lysed with an ammonium chloride solution. The remaining white blood cells were stained with anti-CD45.2-Alexa 488, anti-CD45.1-PE, anti-Ter119-PE-Cy5, anti-Mac-1-PE-Cy7, anti-TCRB-APC, and anti-B220-APC-Cy7. When peripheral blood containing eGFP+ cells was analyzed, anti-CD45.1-Alexa-488 was omitted and anti-Gr-1-PE was used instead of anti-CD45.2-PE if warranted by the experiment. For HSC isolation, bone marrow was first enriched using anti-c-kit beads and immunomagnetic selection was performed on an AutoMACS machine (Miltenyi Biotec). Enriched cells were stained with anti-CD34-FITC, anti-Flk2-PE, anti-lineage (CD3, CD4, CD8, B220, Ter119, Mac-1, Gr-1)-PE-Cy5, anti-Sca-1-PE-Cy5.5, and anti-c-kit-PE-Cy7, and cells were double sorted before transplantation. For analysis of HSC chimerism, CD45.1-APC-Cy5.5 was included, and CD34 staining was achieved with anti-CD34 biotin followed by streptavidin APC. For isolation of HSCs from eGFP-transgenic mice, cells were stained with anti-lineage-Cy5-PE, anti-Sca-1-PE-Cy5.5, anti-c-kit-PE-Cy7, anti-Flk2-PE, and anti-CD34 biotin followed by streptavidin APC. For analysis of eGFP HSC chimerism, anti-CD45.1-APC-Cy5.5 was included.

Immunizations. Mice were immunized intraperitoneally with 100 μg NP conjugated to chicken γ globulin (Biosearch Technologies) precipitated in 10% aluminum potassium sulfate (Sigma-Aldrich). NP-specific enzyme-linked immunosorbent assays were performed with serum obtained 1 wk after immunization on high-protein binding 96-well plates coated with 5 μg NP-BSA (Biosearch Technologies). Wells were developed with anti-mouse IgG-horseradish peroxidase (Southern Biotechnology Associates, Inc.) followed by 1 mg/ml ABTS reagent (Sigma-Aldrich), and the reactions were stopped by the addition of 0.1% sodium azide (Sigma-Aldrich). Absorbance was read at a wavelength of 405 nm.

In vivo depletion of CD4+ T cells. Mice were treated consecutively for 3 d with 500 μg of intravenously injected purified anti-CD4 antibody (GK1.5). Peripheral blood was analyzed for TCRβ and CD8 expression to quantitatively assess CD4+ T cell depletion relative to untreated animals. These mice were then transplanted with 800 GFP+ HSCs 1 d after the third injection. The mice were then given weekly injections of anti-CD4 for the first 3 wk after HSC transplantation and left untreated afterward.

Example 4

HSC Niche Depletion with Imatinib

Animals are initially tested by intravenous administration of a single dose of 10-200 mg/kg imatinib to Rag2−/−γc−/− immunodeficient mice, and the serum tested every two days for the presence of imatinib. The point at which no detectable imatinib is found in the serum is used as the starting point for HSC infusion. To determine whether imatinib administration depletes HSCs in vivo, HSC numbers and frequencies in the bone marrow of treated mice are quantitated at the time of imatinib clearance. Phenotypically identifiable HSCs are identified as KLS CD135− CD150+ cells. Bone marrow HSCs are also identified using expression of Sca-1 and CD150, coupled with the lack of expression of CD34, CD135, CD244, CD48, and CD41 and other antigens associated with lineage commitment.

RAG2−/−(CD45.1) mice are conditioned with 100 mg/kg imatinib, and at time of drug clearance, 5000-10,000 purified c-kit+lineage−Sca-1+ (KLS) CD34−CD150+ HSCs from wild type CD45.2 are introduced into the imatinib conditioned recipients. Peripheral blood is obtained from the recipients every four weeks post transplantation and granulocyte, and lymphocyte chimerism is quantified.

In order to determine the effects of cell dose in this system, RAG2−/−γc−/− (CD45.2) recipient mice are conditioned with 100 mg/kg imatinib as above and transplanted them with varying doses of double-sorted CD45.1 LT-HSCs. Peripheral blood is assayed every four weeks for donor granulocyte chimerism until 24 weeks after transplantation.

Mice. Recipient mice are 4-8 weeks old recombinase activating gene 2-deficient (RAG2−/−), RAG2−/−interleukin-2 common gamma chain deficient (RAG2−/−γc−/−), or μMT mice. Donor mice are 8-12 weeks old GFP transgenic mice expressing GFP from the chicken β-actin promoter, or congenically distinguishable CD45.1 or CD45.2 C57Bl/Ka mice.

HSC Transplantation. Bone marrow was harvested from donor mice by crushing bones, lysing red blood cells with ACK lysis buffer (150 mM NH$_4$Cl, 1 mM KHCO$_3$, and 0.1 mM EDTA), and removing debris on density gradient using Histopaque 1119 (Sigma, St. Louis, Mo.). Bone marrow is c-kit+ enriched using CD117+ microbeads (AutoMACS, Miltenyi Biotec, Auburn, Calif.). Cells were stained with antibodies described below and HSC were isolated by single or double FACS based on previously defined reactivity for particular cell surface markers (c-kit$^+$ lineage$^-$Sca-1$^+$ CD34$^-$ CD150$^+$) on the BD FACS-Aria (BD Biosciences, San Jose, Calif.). Cells were transplanted by retro-orbital injection.

Engraftment Analysis. Blood is obtained from the tail vein of transplanted mice at various time points. It is separated using 2% dextran at 37° C. for 30 min, and subsequently lysed using ACK lysis buffer (150 mM NH4Cl, 1 mM KHCO3, and 0.1 mM EDTA) for 5 minutes. Cells are stained with antibodies described above and analyzed on the BD FACS-Aria. Donor granulocyte chimerism is determined by analyzing the percentage of Ter119$^-$ CD3$^-$ B220$^-$ Mac1$^{high}$side scatter$^{high}$ cells that are also donor$^+$.

A SCID-hu animal model is set up for human bone marrow. The human HSC are tested by conditioning with imatinib for niche depletion as described above, and for chimerism after transplantation.

Scid-hu bone marrow model. Human fetal femurs and tibias (1-2 cm) at 17-22 gestational week (g.w.), which are known to be active in hematopoiesis, are cut along a longitudinal axis so that bone cortex as well as intramedullary regions is exposed. These fragments are then surgically implanted subcutaneously into SCID mice. Homozygous CB-17 scid/scid mice are bred, treated with antibiotics as described (McCune et al., Science (1988) 241:1632), and used when 6-8 weeks old. Methoxyflurane anesthesia is applied during all operative procedures. Hematoxylin-eosin stained tissue sections are prepared from bone grafts 2 weeks and 8 weeks after implantation. The tissues are fixed in 20% formalin, decalcified with EDTA (1.7 mM) in HCl solution, paraffin embedded, and 4 μm sections are cut and stained with hematoxylin and eosin. Grafts are removed at varying intervals after implantation and analyzed for the presence of human hematopoietic activity.

The cell suspensions are prepared from implanted or normal bone marrow tissues, treated with 0.83% of ammonium chloride for 5-10 min at room temperature to lyse red blood cells, and washed with PBS. The cells are incubated with either biotinylated-MEM-43, biotinylated-Ly5.1, or biotinylated control antibodies for 45 min on ice, washed through a fetal bovine serum (FBS) cushion, and then stained with fluorescein conjugated (FITC-) avidin (Caltag Laboratories Inc.) for 45 min. Before flow cytometry, propidium iodide (PI) is added at final concentration of 10 μg/ml to gate out dead cells. Forward and side scattering patterns of the MEM-43 positive cells is obtained by four parameter flow cytometry using a single laser FACScan (Becton Dickinson Immunocytometry Systems).

The human origin of hematopoietic cells within the grafts is confirmed by flow cytometry with either MEM-43 (an antibody specific for a common antigen of human cells) or Ly5.1 (reactive with mouse pan-leukocyte antigen). The replacement of the human bone marrow with mouse hematopoietic cells is observed in some of the grafts incubated in vivo for over 20 weeks.

The characteristics of the hematopoietic cell populations in the bone marrow are analyzed by light scattering profiles using flow cytometry. Four distinctive clusters of hematopoietic cells, i.e., lymphoid (RI), blastoid (R2), myeloid (R3), and mature granulocyte (R4) populations are revealed in normal fetal bone marrow by forward and side scattering distributions. Similar analyses with MEM-43 positive human cells recovered from the bone implants at various different time points after implantation are carried out. Cells recovered 2 weeks after implantation do not show clear cluster formation, indicating that these cells are of non-hematopoietic origin, while the human cells from grafts incubated longer than 4 weeks showed scattering profiles that are similar to those of normal fetal bone marrow cells. Thus, the kinetics of the appearance of human hematopoietic cells in the implanted bone detected by scatter analyses is found to be in accord with the histological observations.

The presence of human cells in the peripheral circulation of SCID-hu mice with bone grafts is examined by FACS analysis, using the combination FITC-HLe1 antibody (the common human leukocyte antigen, CD45) and PE-W6/32 antibody (a monomorphic determinant of MHC-Class I). Human cells are detected at significant frequency in peripheral blood from the SCID-hu mice examined after 9 weeks of implantation.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of hematopoietic stem cell engraftment in a human subject, the method comprising:
   (i) an ablative treatment to ablate endogenous hematopietic stem cells, comprising systemically administering to the subject a monoclonal antibody that specifically binds to human c-Kit at a dose effective to selectively ablate at least 20% of endogenous stem cells in the bone marrow of the subject, in the absence of radiation or chemotherapy;
   (ii) a wash-out period of at least 7 days following administration of the monoclonal antibody that specifically binds to human c-Kit; and
   (iii) transplantation of exogenous hematopoietic stem cells into the subject in a dose effective to achieve long term multilineage peripheral blood chimerism, wherein the transplantation is performed prior to 16 days following the administration of the monoclonal antibody that specifically binds to human c-Kit.

2. The method of claim 1, wherein said exogenous hematopoietic stem cells are allogeneic.

3. The method of claim 1, wherein said exogenous hematopoietic stem cells are autologous.

4. The method of claim 1, wherein said exogenous hematopoietic stem cells are genetically modified stem cells.

5. The method of claim 4, wherein the genetically modified cells were genetically altered by transfection or transduction with a vector or by homologous recombination to express a gene of interest.

6. The method of claim 5, wherein the vector is a virus derived vector.

7. The method of claim 6, wherein the virus is a retrovirus.

8. The method of claim 6, wherein the virus is a lentivirus.

9. The method of claim 4, wherein the genetically modified cells were genetically altered to repair a genetic defect in the human subject.

10. The method of claim 9, wherein said human subject suffers from a genetic blood disorder.

11. The method of claim 10, wherein said genetic blood disorder is a hemoglobinopathy, an aplastic anemia, a sickle cell disease, or a thalassemia.

12. The method of claim 1, wherein the subject has an immunodeficiency.

13. The method of claim 12, wherein the immunodeficiency is a combined immunodeficiency, a severe combined immunodeficiency, Swiss agammaglobulinemia, combined immunodeficiency with adenosine deaminase or nucleoside phosphorylase deficiency, or combined immunodeficiency with immunoglobulins (Nezelof syndrome).

14. The method of claim 1, wherein the subject has a cancer.

15. The method of claim 14, wherein the cancer is chronic lymphocytic leukemia.

16. The method of claim 14, wherein the cancer is breast cancer.

17. The method of claim 1, wherein the antibody that selectively binds c-kit is systemically administered.

18. The method of claim 1, wherein the effective dose of exogenous hematopoietic stem cells is $10^4$ to $10^6$ cells/kg.

19. The method of claim 1, wherein the method provides for up to 90% donor cell chimerism.

20. The method of claim 1, wherein the antibody that selectively binds c-kit is administered in a dose of about 0.1 mg to about 100 mg per day.

\* \* \* \* \*